US010449158B2

(12) United States Patent
Halskov

(10) Patent No.: US 10,449,158 B2
(45) Date of Patent: *Oct. 22, 2019

(54) PHARMACEUTICAL ACTIVATED CARBON COMPOSITION

(71) Applicant: FERRING B.V., Hoofddorp (NL)

(72) Inventor: Soren Halskov, Virum (DK)

(73) Assignee: FERRING B.V., Hoofddorp (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/429,806

(22) PCT Filed: Sep. 20, 2013

(86) PCT No.: PCT/EP2013/069570
§ 371 (c)(1),
(2) Date: Mar. 20, 2015

(87) PCT Pub. No.: WO2014/044794
PCT Pub. Date: Mar. 27, 2014

(65) Prior Publication Data
US 2015/0245999 A1    Sep. 3, 2015

(30) Foreign Application Priority Data

Sep. 21, 2012   (EP) .................................... 12185339
Mar. 25, 2013   (EP) .................................... 13160799

(51) Int. Cl.
| | | |
|---|---|---|
| *A61K 9/00* | (2006.01) | |
| *A61K 33/44* | (2006.01) | |
| *A61P 1/00* | (2006.01) | |
| *A61K 9/50* | (2006.01) | |
| *A61K 9/20* | (2006.01) | |

(52) U.S. Cl.
CPC .......... *A61K 9/5073* (2013.01); *A61K 9/0095* (2013.01); *A61K 9/5026* (2013.01); *A61K 9/5042* (2013.01); *A61K 9/5047* (2013.01); *A61K 33/44* (2013.01); *A61K 9/2081* (2013.01)

(58) Field of Classification Search
None
See application file for complete search history.

(56) References Cited

U.S. PATENT DOCUMENTS

| | | | |
|---|---|---|---|
| 9,682,101 B2 * | 6/2017 | Ekelund | A61K 9/0031 |
| 2001/0051150 A1 | 12/2001 | Ranganathan et al. | |
| 2003/0133978 A1 * | 7/2003 | Davis | A61K 9/0004 424/468 |
| 2004/0166248 A1 * | 8/2004 | Hu | B01J 2/16 427/553 |
| 2008/0031867 A1 * | 2/2008 | Huguet | A61K 9/10 424/94.6 |
| 2008/0254131 A1 * | 10/2008 | Vandse | A61K 9/167 424/490 |
| 2009/0148538 A1 | 6/2009 | Fischer et al. | |
| 2014/0243794 A1 | 8/2014 | Halskov et al. | |

FOREIGN PATENT DOCUMENTS

| | | | | |
|---|---|---|---|---|
| GB | 2012257 A * | 7/1979 | | A61K 33/44 |
| WO | WO 98/22096 A1 | 5/1998 | | |
| WO | WO 2011/104275 A1 | 9/2011 | | |

OTHER PUBLICATIONS

Gunder et al., European Journal of Pharmaceutical Sciences, 1995, 3, 203-214.*
Ruotsalainen, Academic Dissertation, pp. 1-45. (Year: 2003).*
International Search Report dated May 9, 2014 in application No. PCT/EP2013/069570.
Notice of Allowance dated Feb. 22, 2017 in U.S. Appl. No. 14/779,412 (US 2016/0051578).
U.S. Appl. No. 15/598,819, filed May 18, 2017, Ekelund, et al.
Non-Final Office Action issued in co-pending U.S. Appl. No. 15/598,819, dated Aug. 9, 2017.
Office Action dated Jul. 22, 2019 in U.S. Appl. No. 16/123,175 (US 2019-0134081).

* cited by examiner

*Primary Examiner* — Abigail Vanhorn
(74) *Attorney, Agent, or Firm* — Foley & Lardner LLP

(57) ABSTRACT

The invention provides a pharmaceutical composition comprising activated carbon particles, for oral administration. The pharmaceutical composition may be for (use in) the treatment of gastrointestinal fistula.

18 Claims, 6 Drawing Sheets

Fig 2 – adsorption capacity over time from samples tested with phenazone in acidic conditions
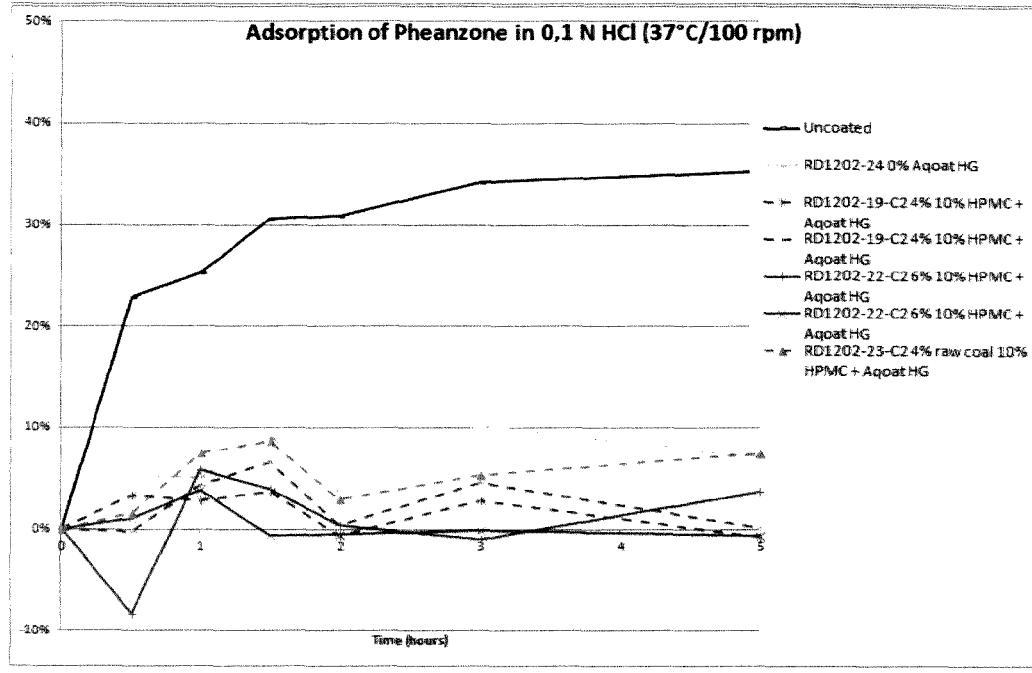
Fig 3 – adsorption capacity over time from samples tested with phenazone at pH=6.8
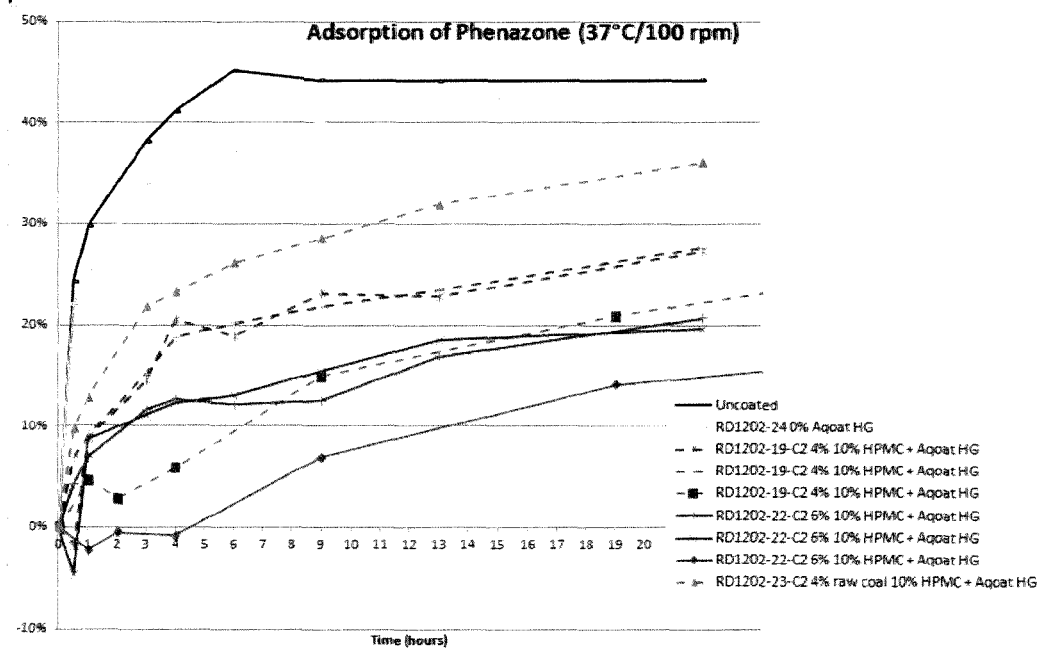

Fig 4 – adsorption capacity over time from samples tested with indole in acidic conditions
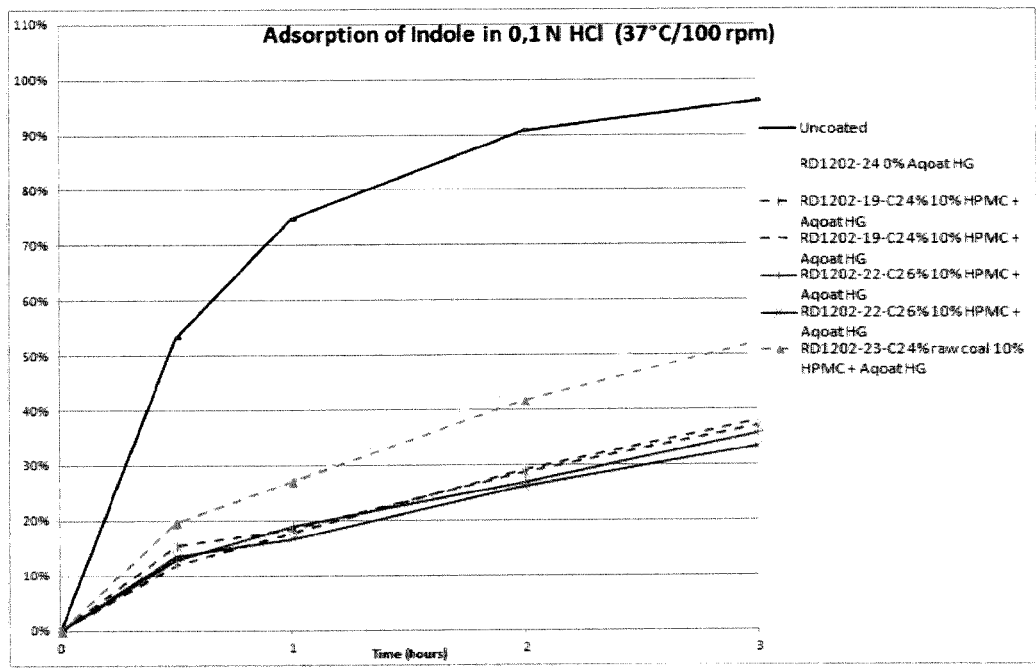
Fig 5 – adsorption capacity over time from samples tested with indole at pH=6.8
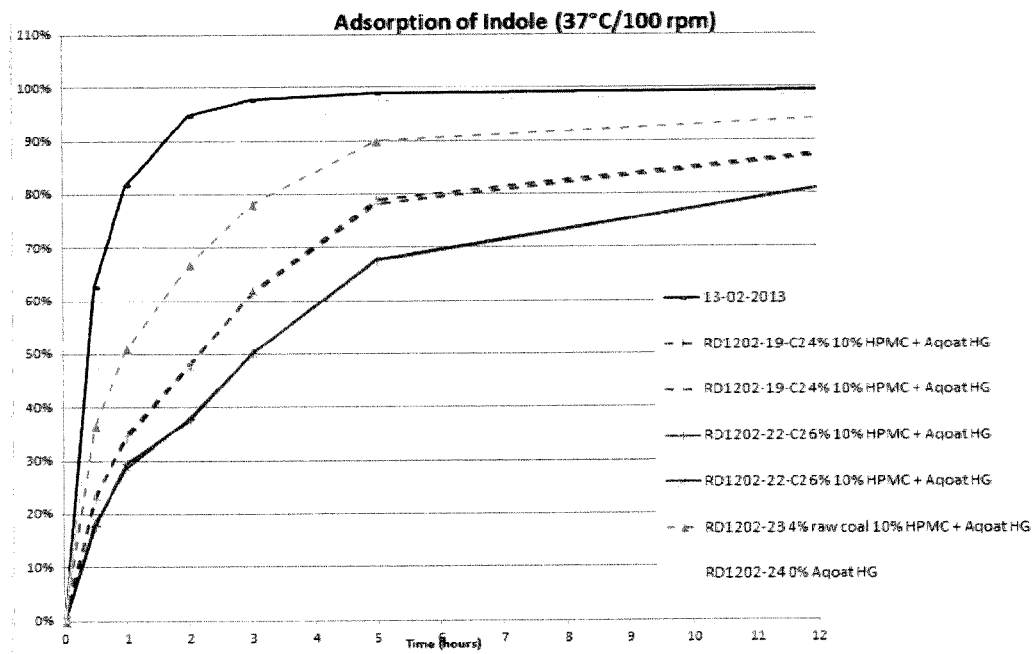

Fig 6 – adsorption capacity over time from samples tested with butyric acid in acidic conditions
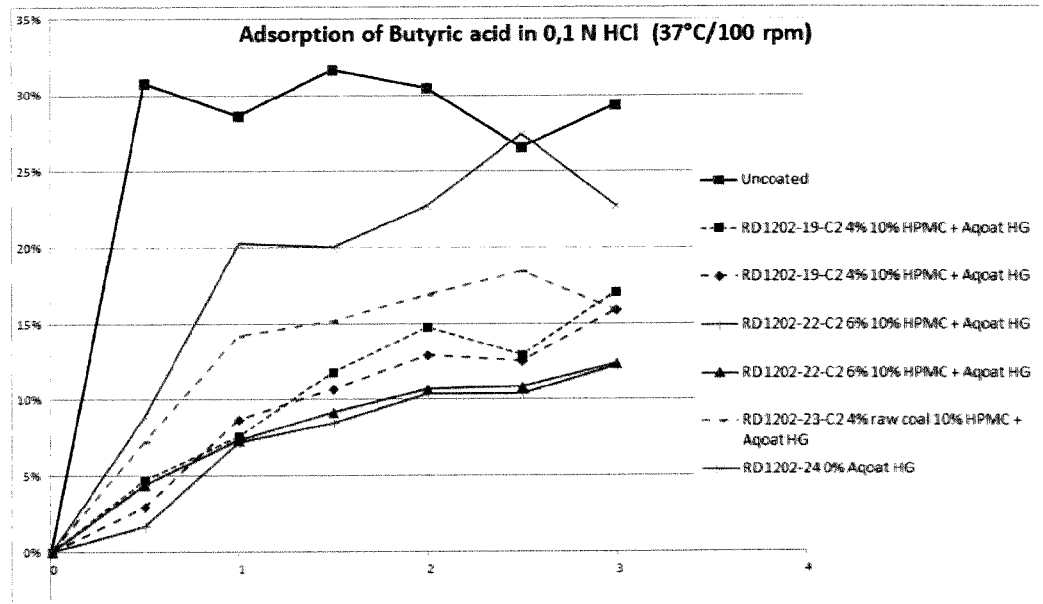
Fig 7 – adsorption capacity over time from samples tested with butyric acid at pH=6.8
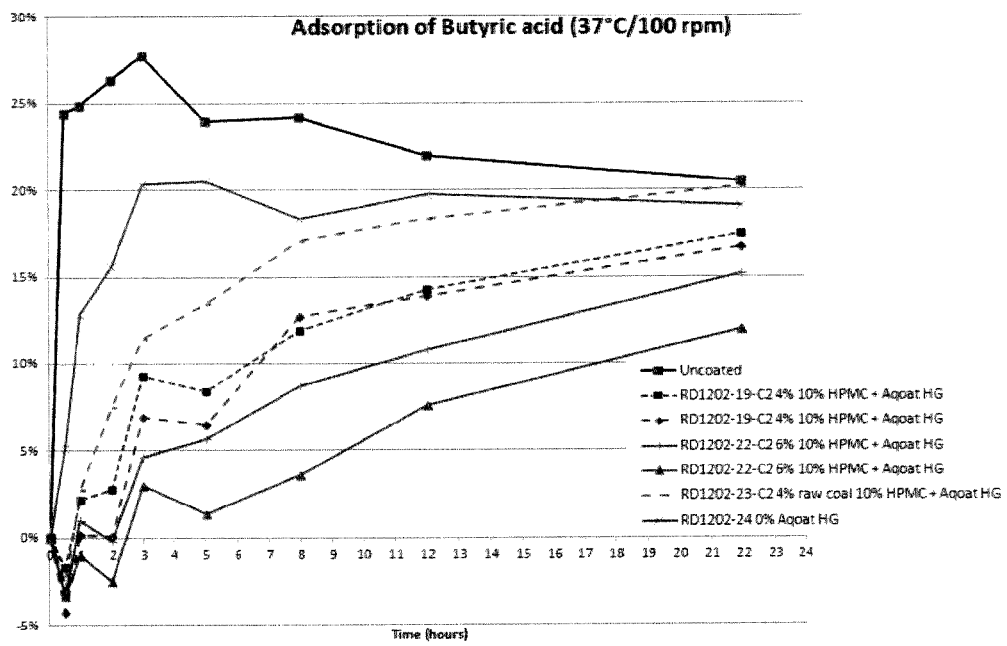

FIGURE 8 shows adsorption capacity over time from samples tested with cholic acid in acidic conditions
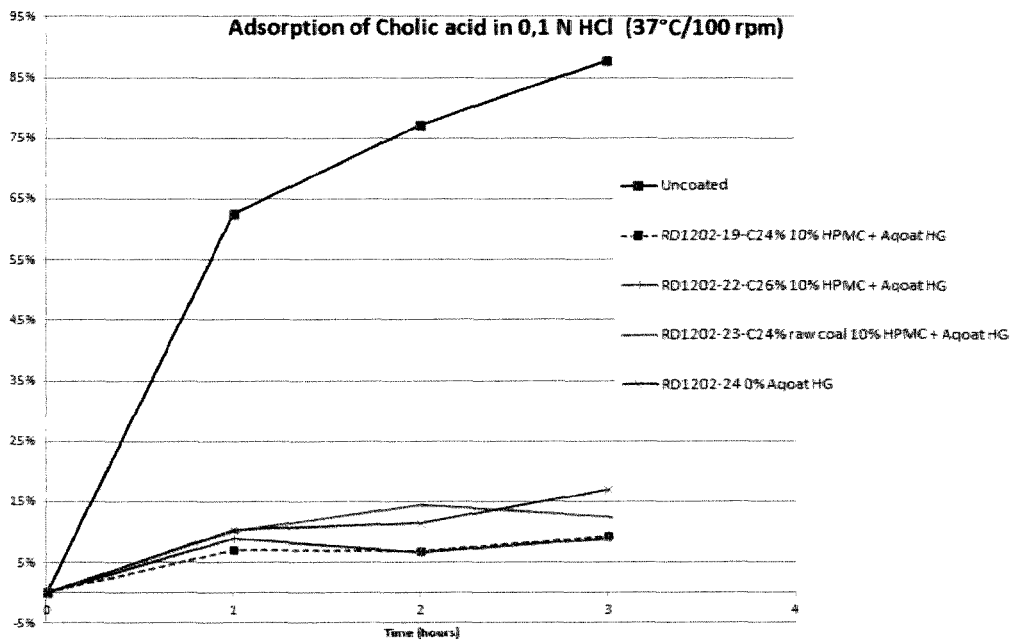
FIGURE 9 shows adsorption capacity over time from samples tested with cholic acid at pH=6.8
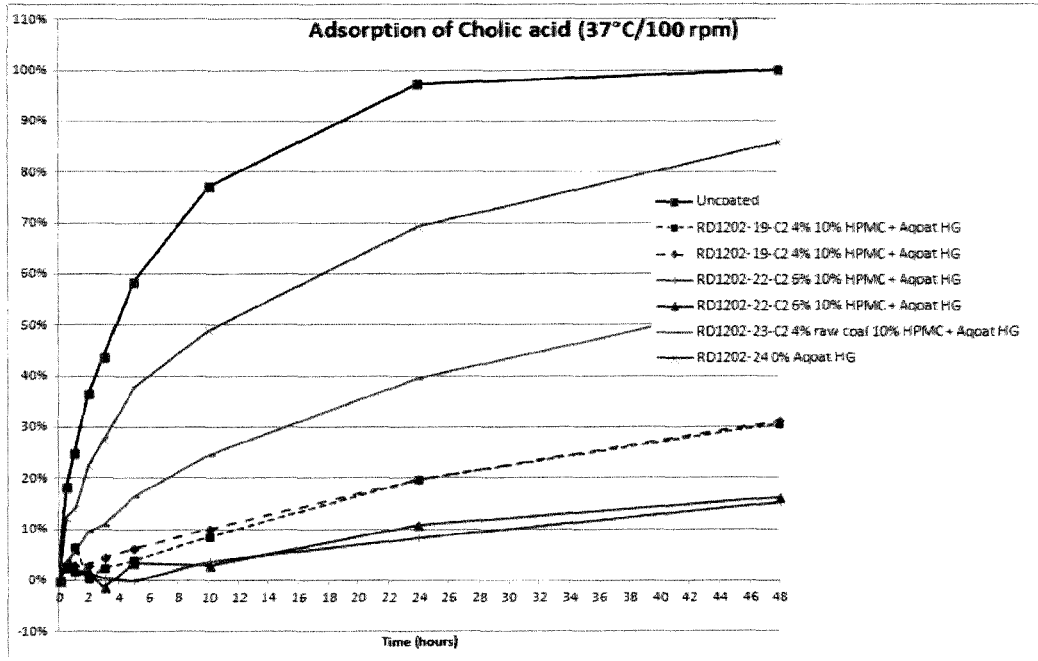

PHARMACEUTICAL ACTIVATED CARBON COMPOSITION

This application claims the benefit of European Patent Application No. 12185339.4 filed 21 Sep. 2012 which is hereby incorporated by reference in its entirety.

The invention relates to a pharmaceutical composition comprising activated carbon particles. The pharmaceutical composition may be for oral administration. The pharmaceutical composition may be for (use in) the treatment of gastrointestinal (GI) dysfunction and/or diseases or malfunction of the GI tract or the like, for example fistula [for example gastrointestinal fistula (e.g. fistula of the lower part of the small intestine, fistula of the large intestine, anorectal fistula)], Irritable Bowel disease, IBD [Ulcerative Colitis or Crohn's disease, Irritable Bowel Syndrome (IBS)]; or for use in the treatment of poisoning (e.g. alcohol poisoning); or for use in reducing or eliminating the side effects of pharmaceutical compositions which are caused when these pharmaceutical compositions or their metabolites (e.g. antibiotics, irinotecan or its metabolite SN38 etc.) are present or build up in the lower ileum, colon or caecum.

BACKGROUND

A fistula is an abnormal conduit or connection between bodily organs or vessels that do not usually connect. Fistulas or fistulae can form in many parts of the body. Anal fistula and rectal fistula are conditions in which tubes form between a sufferer's rectum and intestines, or other internal organs, or between a sufferer's rectum and the external skin adjacent to the sufferer's anus. For example, fistulas situated high in the anus (high anal fistula) may connect with the urinary tract, and fistulas situated low in the anus (low anal fistula) may, in women, pass into the vagina. In addition to significant pain, rectal and anal fistulas commonly become infected and accumulate pus. Furthermore, such fistulas can allow the leakage of fecal matter from the rectum.

Fistulas may form as a result of disease or infection. For example, anal fistulas may arise if a sufferer's anal glands become blocked, thereby forming an abscess that points through from the rectum to the skin surface in the anal region. The growth of fistulas may be accelerated, and fistulas themselves may be maintained, by a local build up of substances which cause irritation (e.g. in the rectum).

Anal and rectal fistulas may be treated by surgical procedures. Such procedures may be undesirable, however. Surgical procedures are generally relatively expensive compared to medication, and are generally less convenient and less preferable to the patient. Further, a potential side-effect of the surgical procedure to treat fistula is an increased probability that a patient will develop anal incontinence in the years following the surgery.

Activated carbon has been proposed for use in the treatment of rectal and anal fistulas. However, there are a number of problems associated with the use of activated carbon for this purpose. Activated carbon is typically supplied as an extremely fine powder having a high surface area. There are problems associated with handling such a powder because the fine scale of the powder particles means the activated carbon tends to contaminate its immediate surroundings with a fine powder dust of activated carbon.

To alleviate some of the handling problems, activated carbon has previously been prepared for oral administration. However, orally administered activated carbon must pass through part of the patient's digestive system before it reaches the affected area, and in doing so a large (and also unpredictable) proportion of the carbon will have adsorbed various chemicals and lost its activity, or otherwise lost its activity, depending on various factors such as amount of food in gut, inter patient variations and day to day variations. By increasing the dose of orally administered activated carbon it may be possible to increase the proportion of carbon that reaches the rectum in an activated state. However, activated carbon absorbs many essential chemicals and nutrients on passing through the patient's digestive system; the long-term administration of large oral doses of activated carbon over a prolonged period is therefore undesirable.

Activated carbon has also been coated or otherwise formulated to allow it to pass through part of the patient's digestive system when taken orally. For example, U.S. Pat. No. 5,554,370 discloses capsules for oral administration of activated carbon. However, it is difficult to prepare a coating that accurately dissolves to release the activated carbon at the affected area. Furthermore, depending on the materials used, coating or encapsulation may itself reduce or eliminate the activity of the carbon (e.g. the carbon may lose its activity very quickly due to adsorption of components of the coating/formulation by the activated carbon) and thereby may reduce the effectiveness of such coated particles.

European Patent Application No. EP11183665.6, and applications claiming priority therefrom, describe formulations of activated carbon suitable for administering activated carbon as a dry dose.

The present disclosure provides an activated carbon composition for oral administration which retains the adsorptive (pharmaceutical) activity of activated carbon following oral administration until it reaches the site of action (e.g. small or large intestine, anus or rectum), and/or which minimises or avoids adsorption of essential chemicals and nutrients by the activated carbon while the composition passes through the patient's stomach etc. to the site of action.

Thus, according to the present invention there is provided a composition (e.g. a pharmaceutical composition) comprising:
(a) a core comprising activated carbon (e.g. activated carbon as the sole active pharmaceutical ingredient);
(b) a first (e.g. an inner) layer around (e.g. surrounding) the core, the first layer comprising an insoluble semipermeable material; and
(c) a second (e.g. outer) layer around (e.g. surrounding) the first layer which breaks down rapidly (e.g. dissolves) at a predetermined pH (e.g. a layer which breaks down rapidly (dissolves) at pH 5 to pH 7, e.g. a layer which breaks down rapidly (e.g. dissolves) at pH 5, a layer which breaks down rapidly (dissolves) at pH≥15.5, a layer which dissolves at pH 7 etc.). It will be appreciated that the second (e.g. outer) layer around (e.g. surrounding) the first layer which breaks down rapidly (e.g. dissolves) at a predetermined pH does not breaks down rapidly (e.g. dissolve) at other pH (e.g. other pH encountered in the GI tract).

According to the present invention in a further aspect there is provided a composition comprising:
(a) a core comprising activated carbon;
(b) a first layer around the core, the first layer comprising an insoluble semipermeable material; and
(c) a second (e.g. outer) layer around (e.g. surrounding) the first layer which dissolves at a predetermined location in the gastrointestinal tract (e.g. the lower part of the small intestine, the colon etc.).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

The following discusses the components of the new compositions described herein in more detail.

(b) the First Layer Around the Core, the First Layer Comprising an Insoluble Semipermeable Material:

The first (e.g. an inner) layer may comprise an insoluble semipermeable membrane.

Herein, the term "semipermeable" means that the material (layer) allows (e.g. gradual) diffusion of molecules and ions through the semipermeable material (layer) towards the core and into contact with the activated carbon and/or allows (e.g. gradual) diffusion of selected molecules and ions through the semipermeable material (layer) towards the core and into contact with the activated carbon. The (e.g. selected) molecules and ions may be materials (e.g. toxins or local irritants) which provoke irritation in the gut (e.g. colon and/or rectum). The (e.g. selected) molecules/ions may be molecules/ions which are produced by the body. The (e.g. selected) molecules and ions may be substances which cause, maintain, promote or exacerbate fistula. The first (e.g. an inner) layer may comprise a material (a semipermeable membrane) which allows (e.g. gradual) diffusion of molecules and ions through the semipermeable material (layer) towards the core and into contact with the activated carbon. Preferably, the (insoluble semipermeable) material does not substantially inactivate the activated carbon.

It will be appreciated that the material of the first layer may be selected based on the molecules and/or ions (e.g. substances which cause, maintain, promote or exacerbate fistula) which are to be adsorbed by the activated carbon (and hence removed by excretion).

The first (e.g. inner) layer comprises an insoluble semipermeable material (e.g. a semipermeable membrane). In examples, the insoluble semipermeable material may be, for example, ethyl cellulose; a poly(meth)acrylate polymer such as EUDRAGIT® RL 100, EUDRAGIT® RL PO, EUDRAGIT® RL 30D, EUDRAGIT® RL 12.5, EUDRAGIT® RS 100, EUDRAGIT® RS PO, EUDRAGIT® RS 30D, EUDRAGIT® RS 12.5, EUDRAGIT® NE 30D, EUDRAGIT® NE 40D, all available from Evonik, glycerylmonostearate, cellulose acetate butyrate, dipolylactic acid, polyvinyl chloride. The first (e.g. inner) layer may further comprise a water soluble material (e.g. a water soluble polymer). The water soluble material (e.g. water soluble polymer) may be mixed with the insoluble semipermeable material (e.g. dispersed within the semipermerable material/membrane). In examples, the water soluble material may be, for example sugar, PVA, PVP, hydroxypropylmethyl cellulose (HPMC), carboxymethylcellulose, sodium carboxymethyl cellulose, salts, sugar alcohols etc. The water soluble material (e.g. water soluble polymer, e.g. HPMC) may be included in an amount which is 0.1 to 30% by weight of the amount of the insoluble semipermeable material (e.g. ethylcellulose) in the layer (b), for example in an amount which is 2 to 25% by weight of the amount of the insoluble semipermeable material (e.g. ethylcellulose) in the layer (b), for example 5 to 15% by weight of the amount of the insoluble semipermeable material in the layer, for example 10% by weight of the amount of the insoluble semipermeable material in the layer.

The water soluble material (e.g. water soluble polymer, e.g. HPMC) may increase the permeability of the insoluble semipermeable material (e.g. ethyl cellulose). For example, dissolution of the water soluble material e.g. HPMC may form defects or channels in the ethyl cellulose coating, when the first layer is exposed after removal of the second (e.g. enteric) layer (see below), to thereby enable the adsorptive capacity of the activated carbon within the layer. Without being bound by theory, it is believed that the channels allow diffusion of material (e.g. substances which cause, maintain, promote or exacerbate fistula etc.) across the first layer, so it may be adsorbed on the activated carbon. The rate of diffusion may therefore be controlled by the amount of water soluble material (e.g. water soluble polymer, e.g. HPMC), and also the thickness of the film; if the film is thinner, there will be a faster diffusion.

The thickness of the first layer around the core may correspond to a theoretical weight increase (of the core) from the layer (film coating) of 1 to 20%, for example 2 to 10%, for example 3 to 7%, for example 4%. It has been found that a coating of around this thickness provides an effective adsorption capacity.

The first (e.g. inner) layer may consist essentially of the insoluble semipermeable material (e.g. ethyl cellulose) and the water soluble material (e.g. water soluble polymer, e.g. HPMC). Avoiding the use of some other ingredients/excipients in the layer (b) prevents loss of adsorptive capacity of the activated carbon to these excipients.

In other examples, the first (e.g. an inner) layer may comprise a mixture of copolymers composed of 85 to 98% by weight free-radical polymerized $C_1$- to $C_4$-alkyl esters of acrylic or methacrylic acid and 15 to 2% by weight (methy) acrylate monomers with a quaternary ammonium group in the alkyl radical. $C_1$- to $C_4$-alkyl esters of acrylic or methacrylic acid are methyl methacrylate, butyl methacrylate, methyl acrylate, ethyl acrylate, butyl acrylate. A preferred (methy) acrylate monomer with a quaternary ammonium group is 2-trimethylammoniummethyl methacrylate chloride.

The first layer may be a copolymer comprising 65% by weight methyl methacrylate, 30% by weight ethyl acrylate and 5% by weight 2-trimethylammoniummethyl methacrylate chloride. Such copolymers are commercially available and known as EUDRAGIT® RS type polymers, for example EUDRAGIT® RS 100, EUDRAGIT® RS PO, EUDRAGIT® RS 30D, EUDRAGIT® RS 12.5 etc., available from Evonik Industries. Preferably, the first layer comprises EUDRAGIT® RS 30 D, available from Evonik Industries.

The first (e.g. an inner) layer may comprise a mixture of copolymers composed of 85 to less than 93% by weight free-radical polymerized $C_1$- to $C_4$-alkyl esters of acrylic or methacrylic acid and 15 to more than 7% by weight 2-trimethylammoniummethyl methacrylate chloride. The first (e.g. an inner) layer may comprise 50 to 70% by weight methyl methacrylate, and 20 to 40% by weight ethyl acrylate.

The first layer may be a copolymer comprising 60% by weight methyl methacrylate, 30% by weight ethyl acrylate and 10% by weight 2-trimethylammoniummethyl methacrylate chloride. Such copolymers are commercially available and known as EUDRAGIT® RL type polymers, for example EUDRAGIT® RL 100, EUDRAGIT® RL PO, EUDRAGIT® RL 30D, EUDRAGIT® RL 12.5 etc., available from Evonik Industries. Preferably, the first layer comprises EUDRAGIT® RL 30 D, available from Evonik Industries.

Preferably, the first (e.g. inner) layer comprises a mixture of a first copolymer comprising 65% by weight methyl methacrylate, 30% by weight ethyl acrylate and 5% by weight 2-trimethylammoniummethyl methacrylate chloride (EUDRAGIT® RS) and a second copolymer comprising 60% by weight methyl methacrylate, 30% by weight ethyl acrylate and 10% by weight 2-trimethylammoniummethyl methacrylate chloride (EUDRAGIT® RL).

The first layer may be EUDRAGIT® NE 30D or EUDRAGIT® NE 40D, available from Evonik.

The amount of the first (e.g. an inner) layer may be 2 to 20% by weight based on the weight of the core with the activated carbon.

(c) the Second Layer Around the First Layer which Dissolves at a Predetermined PH and/or which Dissolves at a Predetermined Location in the Gastrointestinal Tract:

The second (e.g. outer) layer prevents or reduces exposure of the first layer (and the activated carbon) to the digestive system environment, until a predetermined point in the digestive system after the stomach. The second (e.g. outer) layer may, for example, prevent or reduce exposure of the first layer (and the activated carbon) to the digestive system environment, until the composition reaches the lower part of the intestine, i.e. the late ileum, caecum and/or colon. The second layer may be selected from coatings which are pH-sensitive, redox-sensitive or sensitive to particular enzymes or bacteria. It will be appreciated that the mechanism of action of the compositions of the present invention (which holds the activated carbon within the inner membrane/layer) is completely opposite to controlled release formulations where an enteric coating is used to protect an inner layer (as it travels through the stomach) but then dissolves in the intestine to expose the inner layer which immediately releases the active pharmaceutical in the lower digestive tract.

The second layer may be a material which remains substantially intact (e.g. is highly stable, e.g. does not disintegrate or dissolve) at (e.g. highly) acidic pH found in the stomach (e.g. pH 1 to 3), but which breaks down rapidly (dissolves) at less acidic (more basic) pH, for example at pH 5 to 7, e.g. pH 5.5. Preferably the second (e.g. outer) layer is a pH sensitive polymer. The second (e.g. outer) layer may be a polymer which breaks down rapidly (dissolves) at a pH of about 5. The second (e.g. outer) layer may be a polymer which breaks down rapidly (dissolves) at a pH of about 7. The amount of second (e.g. outer) layer (e.g. the enteric layer) may be 2 to 35% or even up to 50% w/w of the total composition, for example the amount of second (e.g. outer) layer (e.g. the enteric layer) may be 8 to 16% w/w of the total composition, for example 10 to 14% w/w of the total composition, for example 12% w/w of the total composition.

The thickness of the second (e.g. outer) layer (e.g. the enteric layer) around the core may correspond to a theoretical weight increase (of the core and first layer) from the film coating of 4 to 16%, for example 6% to 14%, for example 8% or 12%. It was found (see tests below) that such a coating should ensure passage of the stomach prior to exposure of the first layer.

Preferably the second (e.g. outer layer) is an enteric layer. The enteric layer (enteric coating layer) prevents or reduces exposure of the first layer (and the activated carbon) to the digestive system environment, until the composition reaches the small intestine (and even after the composition reaches the small intestine the semipermeable membrane may minimise or prevent adsorption of beneficial substances such as nutrients by the activated carbon).

In some preferred examples, the layer(s) are chosen so the first (inner) layer is exposed in the small intestine, preferably close to the colon (to minimise adsorption of beneficial substances and reserve the bulk of the adsorptive capacity until the colon is reached). Preferably, the enteric layer is a material which remains substantially intact (is highly stable) at (e.g. highly) acidic pH found in the stomach (e.g. pH 1 to 3), but which breaks down rapidly (dissolves) at less acidic (more basic) pH, for example at pH 5 to 7, e.g. pH≥5.5, for example pH 7 as found in small intestine. Preferably the enteric layer (enteric coating layer) is a pH sensitive polymer. The pH sensitive polymer may have a free acid group (carboxylic acid group) with dissolution caused by deprotonation of the acid group. The enteric layer (enteric coating layer) may be a polymer which breaks down rapidly (dissolves) at a pH of about 5. The enteric layer (enteric coating layer) may be a polymer which breaks down rapidly (dissolves) at a pH of about 7. The enteric layer (enteric coating layer) may be a water soluble polymer. The enteric layer may comprise one or more of a methyl acrylate-methacrylic acid copolymer, cellulose acetate succinate, hydroxy propyl methyl cellulose phthalate, hydroxyl propyl methyl cellulose acetate succinate, polyvinyl acetate phthalate (PVAP), methyl methacrylate-methacrylic acid copolymer, sodium alginate and stearic acid. The enteric layer may be a fatty acid, wax, shellac, plastics material etc. The enteric layer may be a pH-dependent enterosoluble polymers, such as cellulose acetate trimellitate (CAT), cellulose acetate phthalate (CAP), anionic copolymers based on methylacrylate, methylmethacrylate and methacrylic acid, hydroxypropyl methylcellulose phthalate (HPMCP), hydroxypropylmethylcellulose acetate succinate (HPMCAS), methacrylic acid and ethyl acrylate copolymers, methacrylic acid and ethyl acrylate copolymers, methacrylic acid and methyl methacrylate copolymers (1:1 ratio), methacrylic acid and methyl methacrylate copolymers (1:2 ratio), Polyvinyl acetate phthalate (PVAP) and Shellac resins. The enteric layer may be EUDRAGIT® E100, E12.5 or E PO. The enteric layer may be, for example, EUDRAGIT® L 100, EUDRAGIT® L 30D, a mixture of EUDRAGIT® S 100/FS 30 D and EUDRAGIT® L 100 (see below). These EUDRAGIT® products are available from Evonik Industries.

The enteric layer may comprise hydroxypropylmethylcellulose acetate succinate (HPMC AS), for example a HMPC AS which dissolves at pH between 5.5 to 6.8. As is known in the art, it is possible to vary the content of acetate and succinate in HPMC AS to provide an enteric coating which dissolves from pH>5.5 to pH>6.8. The enteric layer may consist of, or consist essentially of, hydroxypropylmethylcellulose acetate succinate (HPMC AS), for example a HMPC AS which dissolves at pH between 5.5 to 6.8.

The amount of enteric layer may be 2 to 35% or even up to 50% w/w of the total composition, for example the amount of the enteric layer may be 8 to 16% w/w of the total composition, for example 10 to 14% w/w of the total composition, for example 12% w/w of the total composition.

The thickness of the second (e.g. outer) layer (e.g. the enteric layer) around the core may correspond to a theoretical weight increase (of the core and first layer) from the film coating of 4 to 16%, for example 6% to 14%, for example 8% or 12%. It was found from tests below that such a coating should ensure passage of the stomach prior to exposure of the first layer.

The enteric layer (enteric coating layer) may comprise a copolymer composed of 80 to 95% by weight free-radical polymerized $C_1$- to $C_4$-alkyl esters of acrylic or methacrylic acid and 5 to 25% by weight (meth)acrylate monomers with an anionic group in the alkyl radical. $C_1$- to $C_4$-alkyl esters of acrylic or methacrylic acid are methyl methacrylate, ethyl methacrylate, butyl methacrylate, methyl acrylate, ethyl acrylate, butyl acrylate.

A (meth)acrylate monomer with an anionic group in the alkyl radical may be, for example, acrylic acid or methacrylic acid.

The enteric layer may be a (meth)acrylate copolymer comprising 10 to 30% by weight methyl methacrylate, 50 to 70% by weight methyl acrylate and 5 to 15% by weight methacrylic acid. Such polymers are commercially available and known as EUDRAGIT® FS type polymers. Preferably, the enteric layer comprises EUDRAGIT® FS 30 D, available from Evonik Industries.

The enteric layer may be EUDRAGIT® E100, E12.5 or E PO. The enteric layer may be, for example, EUDRAGIT® L 100, EUDRAGIT® L 30D, a mixture of EUDRAGIT® S 100/FS 30 D and EUDRAGIT® L 100 (see below). These EUDRAGIT® products are available from Evonik Industries.

The amount of the second (enteric) layer may be 5 to 15% by weight based on the weight of the core with the activated carbon and the inner layer.

Preferably the composition or pharmaceutical composition is for oral administration (is orally administrable). The (pharmaceutical) composition may be for (use in) the treatment of gastrointestinal (GI) dysfunction and/or diseases or malfunction of the GI tract or the like, for example fistula [for example gastrointestinal fistula (e.g. fistula of the lower part of the small intestine, fistula of the large intestine, anorectal fistula)], Irritable Bowel disease, IBD [Ulcerative Colitis or Crohn's disease, Irritable Bowel Syndrome (IBS)]; or for use in the treatment of poisoning (e.g. alcohol poisoning); or for use in reducing or eliminating the side effects of pharmaceutical compositions which are caused when these pharmaceutical compositions or their metabolites (e.g. antibiotics, irinotecan or its metabolite SN38 etc.) are present or build up in the lower ileum, colon or caecum.

Preferably the composition (e.g. pharmaceutical composition) is for, or for use in, the treatment of fistula, for example gastrointestinal fistula (e.g. fistula of the small intestine, fistula of the large intestine, anorectal fistula). The composition (e.g. pharmaceutical composition) may be for use in the manufacture of a medicament for the treatment of fistula, for example gastrointestinal fistula (e.g. fistula of the lower part of the small intestine, fistula of the large intestine, anorectal fistula).

While not being limited by any theory, it will be appreciated that examples of the invention may work as follows. The outer (e.g. enteric) layer of the composition remains substantially intact at the acidic pH found in the stomach (e.g. pH 1 to 3), and the pharmaceutical composition therefore remains substantially intact as it travels to and through the stomach following oral administration. However, the outer (e.g. enteric) layer breaks down and dissolves at the pH found in the small intestine (e.g. pH 5 found in the upper part of the small intestine, or pH 7 found in the lower part of the small intestine), thereby exposing the first (e.g. inner) layer. It should be noted that even after the composition reaches the small intestine (and the enteric layer dissolves) the semipermeable membrane (in the first layer) may minimise adsorption of beneficial substances such as nutrients by the activated carbon. In some preferred examples, the layer(s) are chosen so the first (inner) layer is exposed in the lower part of the small intestine, preferably close to the colon (to minimise adsorption of beneficial substances and save the bulk of the adsorptive capacity for the colon). The first layer comprises a material (e.g. a semipermeable membrane) which may allow gradual diffusion of molecules and ions (e.g. materials which irritate the colon or rectum, substances which cause, maintain, promote or exacerbate fistula, etc.) through the semipermeable membrane towards the core into contact with the activated carbon, where they are adsorbed. In some examples, dissolution of a water soluble material (e.g. HPMC) in the semipermeable material (e.g. ethyl cellulose) may form defects or channels in the semipermeable material/layer, when the first (e.g. inner) layer is exposed after removal of the second (e.g. enteric) layer, to thereby slowly enable the adsorptive capacity of the activated carbon within the layer. The (insoluble semipermeable) material does not substantially inactivate the activated carbon, so the activated carbon is available to adsorb these molecules/ions. It will be appreciated that substantially all of the activated carbon is held (remains) within the semipermeable membrane as the composition (minus the outer layer) travels on through the digestive system (e.g. through the lower part of the small intestine and the colon); the activated carbon is not released and is therefore less able to remove (adsorb) essential chemicals such as nutrients.

It will be appreciated that inclusion of the semipermeable membrane (the first, inner, layer) may enable the adsorptive capacity of the activated carbon to be maintained as the composition travels through the whole large intestine [and the formulations may even retain some adsorptive capacity even as they pass through the rectum and anus (i.e. the compositions of the invention may still have adsorptive capacity while they are in the rectum or anus)]. If the semipermeable membrane/first layer were not present the removal of the outer (enteric) layer would make all of the adsorptive capacity of the activated carbon available at once (e.g. at the top of the small intestine), and the amount of adsorptive activity remaining available by the time the composition reached the large intestine may be insufficient to treat the medical condition.

Without wishing to be bound by theory, it is believed that molecules (e.g. toxins or irritants, e.g. substances which cause, maintain, promote or exacerbate fistula) are able to diffuse through the semipermeable membrane where they are adsorbed by the activated carbon and then held on the carbon and subsequently removed by excretion. It will be appreciated that the mechanism of action of the compositions of the present invention (which holds the activated carbon within the inner membrane/layer) is completely opposite to controlled release formulations where an enteric coating is used to protect an inner layer (as it travels through the stomach) but then dissolves in the intestine to expose the inner layer which immediately releases the active pharmaceutical in the lower digestive tract.

The applicants have found that the compositions of the invention may provide a more constant adsorption as they proceed through the gut (after removal of the enteric layer). The retention of adsorptive capacity of activated carbon through the gut (even, depending on the coating used, until the rectum or anus) is important because the exact location of the fistula may not be known and/or because it may be difficult to target the exact site of the fistula.

(a) A Core Comprising Activated Carbon

The core comprises activated carbon. Preferably the core consists of, or consists essentially of, activated carbon. In other words, it is preferred that the core is 100% activated carbon (i.e. activated carbon alone, without other excipients or active ingredients). Thus, preferably the core does not include carrageenan (or a granulation enhancer etc.). The applicants have surprisingly found that it is possible to work with and coat individual granules of activated carbon (e.g. of specific size and/or hardness) without requirement for a granulation excipients such as carrageenan.

The activated carbon is preferably sanded or deburred. Herein, the term "deburred" means untreated "raw" activated carbon is subjected to a finishing process to reduce or minimise the number of tips, peaks and edges (from the surface). The activated carbon may be deburred by the process described below. The active carbon may be deburred or sanded by causing the untreated activated carbon particles to collide with each other at high speed (e.g. speeds from 30 to 300 km/h, for example 35 to 70 km/h). The burred or sanded activated carbon (of specific size) may then be separated for use in/as core (a).

The activated carbon may include 0.9 or fewer tips peaks and edges of height 20-100 μm per particle or granule, for example 0.8 tips or fewer peaks and edges per particle/granule, for example 0.6 tips peaks and edges or fewer per particle/granule, when measured using the microscopy and digital image analysis technique described below.

The activated carbon may be, for example, of particle size 0.02 to 5 mm (depending on the raw material from which the activated carbon is made). The activated carbon may be, for example, of particle size 0.02 to 2.1 mm, for example 0.05 to 2.1 mm, for example 0.1 to 2 mm, for example 0.2 to 2 mm. The activated carbon may be of particle size from 0.6 to 1.2 mm. The activated carbon of this particle size may be selected by sieving the activated carbon (e.g. after it has been sanded/deburred); by selecting activated carbon which includes particles that will pass through a 1.2 mm sieve (i.e. a sieve having aperture size 1.2 mm) but will not pass through a 0.6 mm sieve. Preferably the activated carbon is of particle size from 0.6 to 1.0 mm. The activated carbon of this particle size may be selected by sieving activated carbon (e.g. after it has been sanded/deburred); the preferred activated carbon includes particles that will pass through a 1.0 mm sieve (i.e. a sieve having aperture size 1.0 mm) but will not pass through a 0.6 mm sieve. Herein the term "particle size" means the width at the narrowest point of the activated carbon particle or granule (e.g the diameter for a spherical or roughly spherical particle).

The activated carbon may be made from coconut shells.

Activated carbon (e.g. granular activated carbon) and its methods of manufacture is well known in the art and is available from, for example, Chemviron Carbon.

The applicants have found that activated carbon of particle size between 0.6 to 1.2 mm (e.g. 0.6 to 1.0 mm) and/or which has been sanded or deburred is ready to process (i.e. coat with the first layer); there is no need to granulate/process/extrude/spheronise the carbon or add a granulating agent such as carrageenan. This simplifies the process and means that each core has very high absorption capacity (the core is all activated carbon and there are no excipients etc. present to "dilute" the adsorption capacity). Further, the deburring has the effect of stabilising the adsorbtion rate. Sanding or deburring the raw activated carbon reduces the number of edges (per gram) on the surface of the activated carbon. The raw material is itself very hard to coat consistently, due to the roughness. If the particle is rough, there is high variation in coating thickness over the surface of the overall particle, which has an effect on coating homogeneity and resulting exposure of adsorptive capacity prematurely (e.g. before the colon). Smoothing the activated carbon by sanding or deburring the surface means that the coating thickness is more consistent: the adsorptive capacity of activated carbon is provided in the appropriate place (e.g. in the colon)

The activated carbon may be granular activated carbon. Preferably the core is a granule of activated carbon. It is preferred that the activated carbon particles/granules are formed by grinding or milling carbon material to the desired size. Ground activated carbon has an irregular particle shape. The activated carbon may be in the form of spheronised or spherical particles. The activated carbon may be coated. The activated carbon may be a pharmaceutical or medical grade activated carbon (e.g. activated carbon which complies with Ph. Eur., apart from the particle size).

Preferably the activated carbon is made from coconut shells.

It is preferred that the activated carbon is the sole active pharmaceutical ingredient. Further, it is preferred that the core does not include carrageenan.

The (e.g. pharmaceutical) compositions of the invention may be, may be for use as, or may be for use in the manufacture of, a pharmaceutical formulation or preparation. The pharmaceutical formulation or preparation may, for example, be for, or for use in, the treatment of gastrointestinal (GI) dysfunction and/or diseases or malfunction of the GI tract or the like, for example fistula [for example gastrointestinal fistula (e.g. fistula of the lower part of the small intestine, fistula of the large intestine, anorectal fistula)], Irritable Bowel disease, IBD [Ulcerative Colitis or Crohn's disease, Irritable Bowel Syndrome (IBS)]; the pharmaceutical formulation or preparation may be for, or for use in, the treatment of poisoning (e.g. alcohol poisoning); the pharmaceutical formulation or preparation may be for, or for use in, reducing or eliminating the side effects of pharmaceutical compositions which are caused when these pharmaceutical compositions or their metabolites (e.g. antibiotics, irinotecan or its metabolite SN38 etc.) are present or build up in the lower ileum, colon or caecum.

The (e.g. pharmaceutical) compositions may be used to treat patients who are also receiving activated carbon administered rectally.

According to the present invention in a further aspect there is provided a pharmaceutical formulation or preparation comprising one or more (e.g. a plurality) of compositions according to any aspect of the invention. The pharmaceutical formulation or preparation may comprise one, or generally very many more, compositions according to the invention, each comprising a core (e.g. granule of activated carbon), inner layer and outer layer. In this example the pharmaceutical formulation or preparation (which may comprise tens or hundreds of such compositions) may be administered as a powder or granules, as a microparticulate formulation, or suspended in a pharmaceutically acceptable solution. The pharmaceutical formulation or preparation may comprise one or more compositions [each comprising a core (e.g. granule of activated carbon), inner layer and outer layer] e.g. which are formulated in a dosage form, e.g. an oral dosage form, e.g. a tablet or capsule. In an example, a pharmaceutical formulation or preparation is in the form of a capsule which includes 400 mg of the composition(s) of the invention. The pharmaceutical formulation or preparation may comprise additional components such as dryers (such as alumina, aerosils etc.), release agents, stabilizers, colourants, antioxidants, wetting agents, pigments, gloss agents, plasticisers, disintegrants etc. The use of these agents (and the amount required) is well known and customary in the art.

According to the present invention a composition (e.g. a pharmaceutical composition) comprises:

(a) a core comprising activated carbon (e.g. activated carbon as the sole active pharmaceutical ingredient, e.g. sanded/deburred activated carbon, e.g. activated carbon of particle size 0.6 to 1.0 mm);

(b) a first (e.g. an inner) layer around (e.g. surrounding) the core, the first layer comprising an insoluble semipermeable material in the form of ethyl cellulose, and optionally further comprising a water soluble material in the form of hydroxypropylmethylcellulose (HPMC);

(c) a second (e.g. outer) layer comprising hydroxypropylmethylcellulose acetate succinate (HPMC AS).

In an example, the composition (pharmaceutical composition) comprises:

a) a core comprising (e.g. which is) activated carbon;

b) an inner layer (coating) of a copolymer or of a mixture of copolymers composed of 85 to 98% by weight free-radical polymerized C1- to C4-alkyl esters of acrylic or methacrylic acid and 15 to 2% by weight (methy) acrylate monomers with a quaternary ammonium group in the alkyl radical; and c) an outer layer (coating) of a copolymer composed of 80 to 95% by weight free-radical polymerized $C_1$- to $C_4$-alkyl esters of acrylic or methacrylic acid and 5 to 25% by weight (meth)acrylate monomers with an anionic group in the alkyl radical.

The composition (pharmaceutical composition) may comprise:

a) a core comprising (e.g. which is) activated carbon;

(b) an inner layer (coating) comprising a mixture of a first copolymer comprising 65% by weight methyl methacrylate, 30% by weight ethyl acrylate and 5% by weight 2-trimethylammoniummethyl methacrylate chloride (EUDRAGIT® RS, e.g. EUDRAGIT® RS 30D) and a second copolymer comprising 60% by weight methyl methacrylate, 30% by weight ethyl acrylate and 10% by weight 2-trimethylammoniummethyl methacrylate chloride (EUDRAGIT® RL, e.g. EUDRAGIT® RL 30D); and (c) an outer (enteric) layer (coating) comprising a (meth) acrylate copolymer comprising 10 to 30% by weight methyl methacrylate, 50 to 70% by weight methyl acrylate and 5 to 15% by weight methacrylic acid (EUDRAGIT® FS, e.g. EUDRAGIT® FS 30 D).

Preferably the core is activated carbon. In other words, it is preferred that the core is 100% activated carbon (i.e. activated carbon alone, without other excipients or active ingredients). The core may be a granule of activated carbon. The compositions of the invention may further comprise additional components such as dryers (such as alumina, aerosils etc.), release agents, stabilizers, colourants, antioxidants, wetting agents, pigments, gloss agents, plasticisers etc. The use of these agents (and the amount required) is well known and customary in the art.

The pharmaceutical compositions described herein may be used for the treatment of a gastrointestinal (GI) dysfunction and/or diseases or malfunction of the GI tract or the like, for example fistula [for example gastrointestinal fistula (e.g. fistula of the lower part of the small intestine, fistula of the large intestine, anorectal fistula], Irritable Bowel disease, IBD [Ulcerative Colitis or Crohn's disease, Irritable Bowel Syndrome (IBS)]; for the treatment of poisoning (e.g. alcohol poisoning); or for treatment to reduce or eliminate the side effects of pharmaceutical compositions which are caused when these pharmaceutical compositions or their metabolites (e.g. antibiotics, irinotecan or itrs metabolite SN38 etc.) are present or build up in the lower ileum, colon or caecum. The methods of treatment include administering (e.g. orally) to a patient in need thereof a (pharmaceutically effective amount of a) composition (e.g. a pharmaceutical composition) as described herein.

According to the present invention in a further aspect there is provided a method of treatment of gastrointestinal (GI) dysfunction and/or diseases or malfunction of the GI tract or the like, for example fistula [for example gastrointestinal fistula (e.g. fistula of the lower part of the small intestine, fistula of the large intestine, anorectal fistula)]. Irritable Bowel disease, IBD [Ulcerative Colitis or Crohn's disease, Irritable Bowel Syndrome (IBS)]; a method of treatment of poisoning (e.g. alcohol poisoning); or a method of treatment to reduce or eliminate the side effects of pharmaceutical compositions which are caused when these pharmaceutical compositions or their metabolites (e.g. antibiotics, irinotecan or its metabolite SN38 etc.) are present or build up in the lower ileum, colon or caecum; the method, comprising a step of administering (e.g. orally) to a patient in need thereof a (pharmaceutically effective amount of a) composition (e.g. a pharmaceutical composition) comprising:

(a) a core comprising activated carbon (e.g. activated carbon as the sole active pharmaceutical ingredient);

(b) a first (e.g. an inner) layer around (e.g. surrounding) the core, the first layer comprising an insoluble semipermeable material; and (c) a second (e.g. outer) layer around (e.g. surrounding) the first layer which breaks down rapidly (dissolves) at a predetermined pH (e.g. a layer which breaks down rapidly (dissolves) at pH 5 to pH7, e.g. a layer which breaks down rapidly (dissolves) at pH 5, a layer which breaks down rapidly (dissolves) at pH≥5.5, a layer which dissolves at pH 7 etc.) and/or which dissolves at a predetermined location in the gastrointestinal tract.

Preferably the core is activated carbon. In other words, it is preferred that the core is 100% activated carbon (i.e. activated carbon alone, without other excipients or active ingredients). The core may be a granule of activated carbon.

The treatment may comprise administration of an effective dose of activated carbon of 50 mg to 10 g activated carbon, for example 100 mg to 5 g activated carbon, for example 100 mg to 4 g activated carbon. The treatment may comprise administration of a total dose of 50 mg to 10 g activated carbon, for example 100 mg to 5 g activated carbon, for example 100 mg to 4 g (e.g. 3.2 g) activated carbon, per day. The total dose may be administered in a single dose, or may be divided into more than one dose, per day. The skilled person would readily understand, based on the weight of the composition and the weight of activated carbon therein, the amount of the composition (which of course includes a certain amount of other components) required to achieve these effective doses.

The fistula may be, e.g. gastrointestinal fistula (e.g. fistula of the small intestine, fistula of the large intestine, anorectal fistula).

The method may comprise a step of administering (e.g. orally) a composition (pharmaceutical composition) comprising:

a) a core comprising activated carbon;

b) an inner layer of a copolymer or of a mixture of copolymers composed of 85 to 98% by weight free-radical polymerized C1- to C4-alkyl esters of acrylic or methacrylic acid and 15 to 2% by weight (methy) acrylate monomers with a quaternary ammonium group in the alkyl radical; and c) an outer layer of a copolymer composed of 80 to 95% by weight free-radical polymerized $C_1$- to $C_4$-alkyl esters of acrylic or methacrylic acid and 5 to 25% by weight (meth) acrylate monomers with an anionic group in the alkyl radical.

The method may comprise a step of administering (e.g. orally) a composition (pharmaceutical composition) comprising:

a) a core comprising activated carbon;

(b) an inner layer comprising a mixture of a first copolymer comprising 65% by weight methyl methacrylate, 30% by weight ethyl acrylate and 5% by weight 2-trimethylammoniummethyl methacrylate chloride (EUDRAGIT® RS, e.g. EUDRAGIT® RS 30D) and a second copolymer comprising 60% by weight methyl methacrylate, 30% by weight ethyl acrylate and 10% by weight 2-trimethylammoniummethyl methacrylate chloride (EUDRAGIT® RL, e.g. EUDRAGIT® RL 30D); and (c) an outer (enteric) layer comprising a (meth)acrylate copolymer comprising 10 to 30% by weight methyl methacrylate, 50 to 70% by weight methyl acrylate and 5 to 15% by weight methacrylic acid (EUDRAGIT® FS, e.g. EUDRAGIT® FS 30 D).

Preferably the core is activated carbon. In other words, it is preferred that the core is 100% activated carbon (i.e. activated carbon alone, without other excipients or active ingredients). The core may be a granule of activated carbon. The composition may be administered as a powder, granules, suspension, tablet, capsule etc.

According to the present invention in a further aspect there is provided a method of treatment of gastrointestinal (GI) dysfunction and/or diseases or malfunction of the GI tract or the like, for example fistula [for example gastrointestinal fistula (e.g. fistula of the lower part of the small intestine, fistula of the large intestine, anorectal fistula)], Irritable Bowel disease, IBD [Ulcerative Colitis or Crohn's disease, Irritable Bowel Syndrome (IBS)]; a method of treatment of poisoning (e.g. alcohol poisoning); or a method of treatment to reduce or eliminate the side effects of pharmaceutical compositions which are caused when these pharmaceutical compositions or their metabolites (e.g. antibiotics, irinotecan or its metabolite SN38 etc.) are present or build up in the lower ileum, colon or caecum; the method, comprising a step of administering (e.g. orally) to a patient in need thereof a composition (e.g. a pharmaceutical composition) comprising:

(a) a core comprising activated carbon (e.g. activated carbon as the sole active pharmaceutical ingredient, e.g. sanded/deburred activated carbon, e.g. activated carbon of particle size 0.6 to 1.0 mm);

(b) a first (e.g. an inner) layer around (e.g. surrounding) the core, the first layer comprising an insoluble semipermeable material in the form of ethyl cellulose, and optionally further comprising a water soluble material in the form of hydroxypropylmethylcellulose (HPMC);

(c) a second (e.g. outer) layer comprising hydroxypropylmethylcellulose acetate succinate (HPMC AS).

The fistula may be, e.g. gastrointestinal fistula (e.g. fistula of the small intestine, fistula of the large intestine, anorectal fistula). The treatment may comprise administration of an effective dose of activated carbon of 50 mg to 10 g activated carbon, for example 100 mg to 5 g activated carbon, for example 100 mg to 4 g activated carbon. The treatment may comprise administration of a total dose of 50 mg to 10 g activated carbon, for example 100 mg to 5 g activated carbon, for example 100 mg to 4 g (e.g. 3.2 g) activated carbon, per day. The total dose may be administered in a single dose, or may be divided into more than one dose, per day. The skilled person would readily understand, based on the weight of the composition and the weight of activated carbon therein, the amount of the composition (which of course includes a certain amount of other components) required to achieve these effective doses.

DETAILED DESCRIPTION OF THE INVENTION

The present invention will now be illustrated with reference to the following examples and attached drawings in which:

FIG. 2 shows adsorption capacity over time from samples tested with phenazone in acidic conditions;

FIG. 3 shows adsorption capacity over time from samples tested with phenazone at pH 6.8;

FIG. 4 shows adsorption capacity over time from samples tested with indole in acidic conditions;

FIG. 5 shows adsorption capacity over time from samples tested with indole at pH=6.8;

FIG. 6 shows adsorption capacity over time from samples tested with butyric acid in acidic conditions;

FIG. 7 shows adsorption capacity over time from samples tested with butyric acid at pH=6.8;

FIG. 8 shows adsorption capacity over time from samples tested with cholic acid in acidic conditions;

Figure 10:
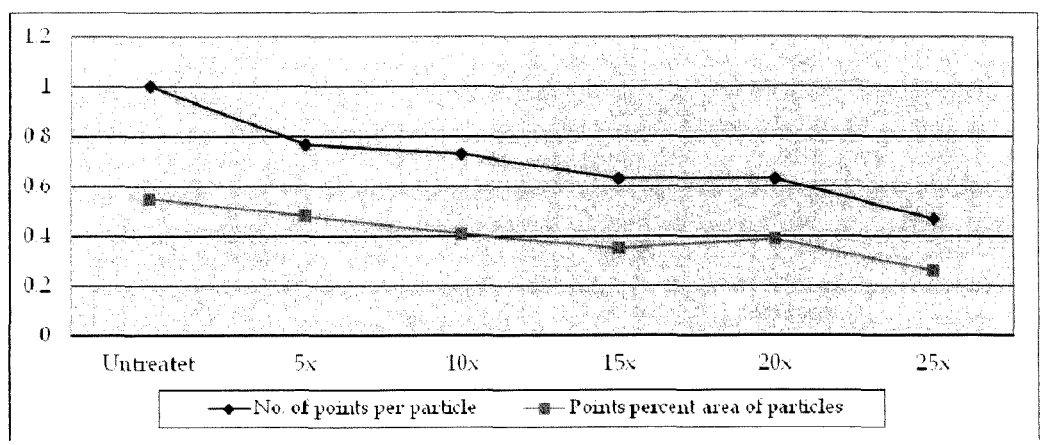

FIG. 9 shows adsorption capacity over time from samples tested with cholic acid at pH=6.8; and FIG. 10 shows the reduction in number of tips, peaks and edges in activated carbon subjected to the deburring process described below, shown by the microscopy and digital image analysis technique described below. The top line (diamonds) shows the number of tips per particle, and the bottom line (squares) shows the percentage area of tips, for untreated activated carbon, and for activated carbon which has been passed through the apparatus of FIGS. 1A and 1B described below 5, 10, 15, 20 or 25 times.

A. THE COMPONENTS OF THE COMPOSITION

The composition (e.g. pharmaceutical composition) of the invention comprises:

(a) a core comprising activated carbon (e.g. activated carbon as the sole active pharmaceutical ingredient);

(b) a first (e.g. an inner) layer around (e.g. surrounding) the core, the first layer comprising an insoluble semipermeable material; and (c) a second (e.g. outer) layer around (e.g. surrounding) the first layer which breaks down rapidly (dissolves) at a predetermined pH (e.g. a layer which breaks down rapidly (dissolves) at pH 5 to pH 7) or which dissolves at a predetermined location in the gastrointestinal tract.

The following deals with each layer in turn.

(a) A Core Comprising Activated Carbon

Activated Carbon and its Production

To assure the suitability of the activated carbon starting material for processing into a final uniform and reproducible product, the activated carbon starting material is subjected to a pre-treatment process. The objective of this pre-treatment is to reduce the number of burrs, tips and sharp edges because these will negatively impact the quality of the first (and second) layers which are applied to the surface of the activated carbon. A burr, tip or sharp edge is more difficult to cover with a uniform layer of coating material, hence particles are subjected to mechanical erosion to form a more uniform surface.

Figure 1A:
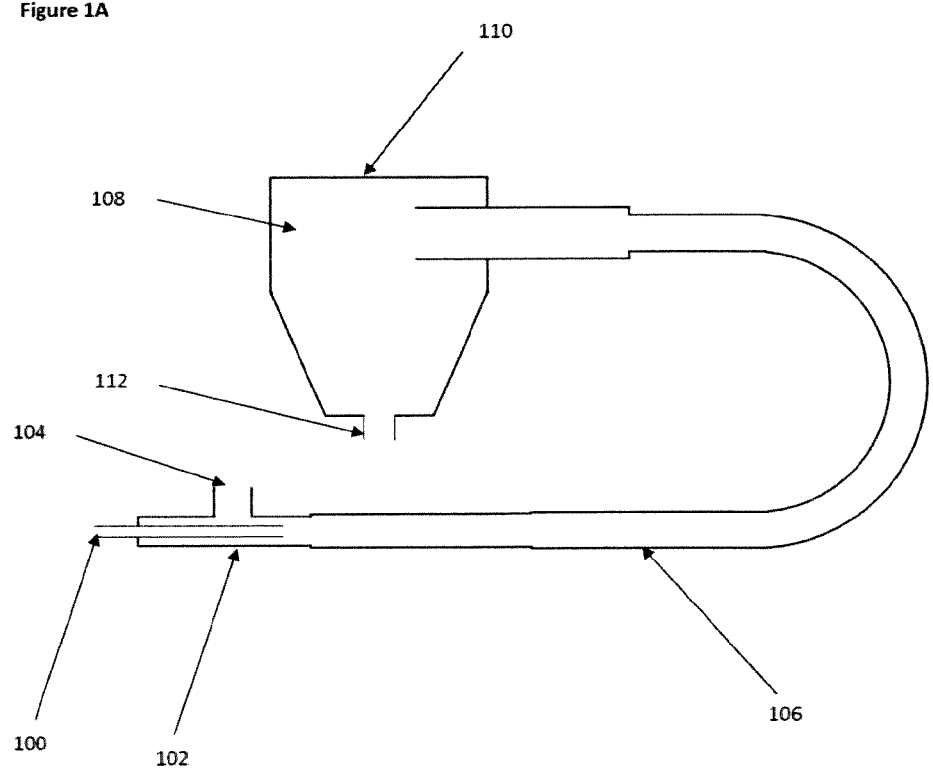
FIGS. 1A and 1B shows top and side views of an apparatus for pretreating (sanding/deburring) activated carbon for use in formulations according to the invention.
Figure 1B:
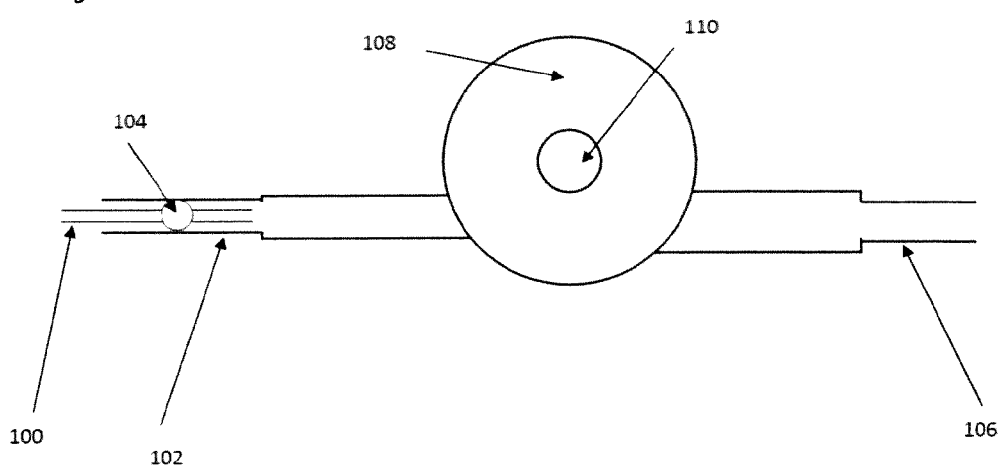

In this example the process involves the equipment shown in FIGS. 1A and 1B. The principle of this process is to mechanically erode burrs, tips or edges on the individual carbon particles by having them colliding with one another at high speed when passing through a collision tube, followed by a sieving process to achieve particles of adequate size distribution.

The starting material activated carbon is made from coconut shells (Chemviron Carbon, Lockett Road, Ashton-In-Makerfield, Lancashire WN4 8DE UK product name AQUACARB 607C 14×40 having a particle size from 1.40 mm to 0.425 mm). This quality of activated carbon starting material will, when subjected to the below described instrumental set up by the described instrumental parameters, result in a product, having suitable properties for being further processed into the final coated product with the desired properties.

The mechanically erosion of the carbon particle is done in the equipment shown in FIGS. 1A and 1B. The instrument is fully in pharmaceutical stainless steel quality 316.

On the instrument, a high pressure (in this case 8 bar) is applied to a small inner-tubing 100. This inner-tubing is inserted in a larger outer-tubing having a larger diameter. A heavy airstream, in this case approx. 21 m$^3$/h in the small inner-tube will thus be injected into the outer-tube 102, creating a jet air-flow through this tube. At inlet 104, before the airflow from the inner-tube is led into the outer-tube, a vacuum will arise creating a flow of in this case approx. 35 m$^3$/h. The first part of the outer-tube serves as a collision tube and is connected to a tube with higher diameter 106. To make the instrument more compact, the tube 106 in this case has a curvature diverting the airstream (180°) and let into a cyclone 108. Active carbon starting material is gradually fed into the tubing at inlet 104, in this case at a rate of 2 kg/min. The carbon particles will in this case gain a velocity of around 70 km/h in the first part of the collision tube and carbon particles will collide with each other resulting in any sharp edges and burrs being eroded. The velocity of the particles will decline as the diameter of the outer-tube is enlarged in this case to around 35 km/h at the inlet to the cyclone. Extract ventilation is applied to the top of the cyclone at 110 and regulated to balance the incoming air, so the net airflow is nearly zero at the bottom outlet 112 of the cyclone at. Small carbon particles and fragments are removed by ventilation from the top of the cyclone 110, while larger particles are collected at the outlet 112 at the bottom of the cyclone. After collection of the larger particles, the process may be repeated several times by introducing the collected particles into the system again at inlet 104 until the carbon particles are sufficiently eroded for further processing. After completing the erosion process, the collected particles are now subjected to a vibration sieve in portions of 200 g and sieved through a 1.0 and subsequently a 0.6 mm sieve. The fraction passing the 1.0 mm sieve and not the 0.6 mm sieve has an acceptable particle size and shape to be used as starting material for coating processes.

In the current example, 2125 g of activated carbon was introduced in the process. 2003 g of carbon was collected after repeating the erosion process for 25 times. A loss of 6% smaller particles and fragments was noticed. Following sieving, the useful product fraction (0.6<p<1.0) yielded 924 g The pre-treatment process had after correcting for sampling, an overall yield of approx 48% in this example.

The useful product fraction is coated as set out below.

Testing the Surface of the Activated Carbon

Macroscopy and digital image analysis may be used to assess the effect of the deburring process. Using digital image analysis it is possible to characterize the shape of the individual particles and small points of roughness or tips can be identified. The technique is based upon being able to detect even very small tips (typically in the range from approximately 20-100 μm). The measurement utilizes a macro scope with a low magnification (approximately 4×) and acquiring images with a digital camera. The images are analyzed using digital image analysis software (Media Cybernetics Image Pro-Plus version 6.1.0.346). The detailed settings are specified in the attached appendix I.

The procedure is that the particles are first converted to a black and white mask. The particles are then measured with regards to area. After this the images are treated with a function to even out small tips called 2×21 square, close, 6 passes. The area of the particle in the treated image is measured. To obtain the tips, the treated image is subtracted from the untreated. The resulting image contains the tips and also some residual noise. The residual noise is removed using a function called 2×2 square open, 1 pass. The resulting particles are the tips.

A number of samples have been analyzed to evaluate if the analytical procedure can differentiate between coal particles having been processed increasingly number of times. Particles having been processed (by the apparatus of FIGS. 1A and 1B) 0, 5, 10, 15, 20 and 25 times have been analyzed. The results have been evaluated with regards to number of tips and % area of tips. FIG. 10 shows the reduction in number of tips, peaks and edges in activated carbon subjected to the deburring process, shown by the microscopy and digital image analysis technique described above. The top line (diamonds) shows the number of tips/points per particle, and the bottom line (squares) shows the percentage area of tips/points, for untreated activated carbon, and for activated carbon which has been passed through the apparatus of FIGS. 1A and 1B either 5, 10, 15, 20 or 25 times. As can be seen, the untreated activated carbon has 1 tip per particle, but this decreases with the number of passages through the apparatus (e.g. after passage through the apparatus 5 times there are 0.77 tips per particle, after passage through the apparatus 10 times there are 0.73 tips per particle, after passage through the apparatus 15 times there are 0.63 tips per particle, after passage through the apparatus 20 times there are 0.63 tips per particle, after passage through the apparatus 25 times there are 0.47 tips per particle etc.

As expected, the number of tips decreases with increasing number of treatments. This correlation is also in good agreement with what has been observed, i.e. that the more times the particles are treated, the more complete is the coating.

(b) the First Layer Around the Core, the First Layer Comprising an Insoluble Semipermeable Material:

It was a target to develop film compositions with a minimum of additives (especially for the inner film) to minimise take up of adsorptive capacity by additives. The first (e.g. an inner) layer may therefore consist essentially of the insoluble semipermeable material (e.g. ethyl cellulose) and (optionally) the water soluble material (e.g. HPMC). Avoiding other ingredients/excipients prevents loss of adsorptive capacity of the activated carbon to these excipients. The simplest film would be an ethylcellulose film (insoluble semipermeable material alone) applied from an ethanol solution. It was expected that this film would be very tight, not allowing sufficient/efficient passage of unwanted substances. Thus, to ensure that the adsorption capacity of activated carbon is made available/accessible, different water soluble materials (e.g. water soluble polymers) were mixed into the ethylcellulose to make holes in it or make it dissolve (on exposure to the pH in the lower intestine/colon). Polyvinylpyrrolidone (PVP), Hypromellose (HPMC) and Polyvinyl alcohol (PVA) were used as water soluble polymers. PVP is both soluble in water at ethanol, HPMC only in water. Low viscosity grades of PVP and HPMC were chosen (Kollidon K30 and Pharmacoat 603 respectively) in order not to influence the coating process with highly viscous film solutions.

For the following examples, the film coating was performed by methods well known in the art, in a GEA Aeromatic Fielder Strea 1 fluid-bed installed with a wurster tube. Liquid was pumped with a peristaltic pump. As Hypromellose (HPMC) is not soluble in Ethanol and Ethylcellulose is not soluble in water, the ethanol/water mix at which both polymers can dissolve was found to be between 70:30 and 80:20. The mix 75:25 was chosen as standard in the film (first layer) formulations with Ethylcellulose combined with Hypromellose.

The first layer was added by the above methods, to provide compositions according to the invention as set out in the Tables below.

(c) The Second Layer Around the First Layer which Dissolves at a Predetermined PH and/or which Dissolves at a Predetermined Location in the Gastrointestinal Tract:

For the enteric coating, a polymer with release at higher pH was selected, aiming at having the activated carbon available as close to the colon as possible. On the other hand, choosing an enteric coating with release at a too high pH could mean that the activated carbon would not be available in all patients (because gut pH and transit time can vary considerably from patient to patient and day to day). Based on this, Aqoat HG (HPMC-AS; Hypromellose-Acetate-Succinate; releases at pH 6.5) was chosen for the examples. Alternatives could be e.g. other Aqoat products (which release at other pH values), mixtures of Eudragit S 100/FS 30 D and Eudragit L 100 to reduce the release from pH 7.0 resulting from using Eudragit S 100/FS 30 D alone.

The amount of enteric layer in the following examples is 8 to 16% w/w of the total composition, for example 10 to 14% w/w of the total composition, for example 12% w/w of the total composition.

For the following examples, the film coating was performed by methods well known in the art, in a GEA Aeromatic Fielder Strea 1 fluid-bed installed with a wurster tube. Liquid was pumped with a peristaltic pump.

The second layer was added by the above methods, to provide compositions according to the invention as set out in the Tables below.

EXAMPLES

The invention is further described in the following examples, which do not limit the scope of the invention described in the claims.
Testing Compositions of the Invention
Analytical Methods
Adsorption Capacity The development and testing of formulations was based on model chemicals. The choice of model chemical adsorbants should reflect different types of chemical structure and preferably they should be relevant to the human digestional tract. The model adsorbants for this work were:

Phenazone: Phenazone is a water soluble (51.9 g/L) analgesic which is used to determine the adsorption capacity of activated carbon as described in Ph. Eur (2005:0313). Phenazone has a molar mass of 188.2 g/mol, pka of 1.5 and a Log P of 0.38. It is therefore a polar chemical which is not ionized in the stomach. Phenazone is not normally found in the GI tract but was used as it is used in the pharmacopeia method for adsorption.

Indole: Indole is an aromatic heterocyclic organic compound which is a precursor for many pharmaceuticals. Indole can be produced by bacteria as a degradation product of the amino acid tryptophan. It occurs naturally in human feces at levels of approximately 100 mg/l and has an intense fecal odor. Indole has a molar mass of 116.14 g/mol, solubility in water is 3.56 mg/mL and the pKa is reported as 16.22. Indole is therefore a more lipid soluble compound compared to Phenazone (Log P=2.14), and not ionized in the GI tract.

Butyric acid: Butyric acid is a short chain fatty acid found in milk, butter and cheese, and as a product of anaerobic fermentation for instance in the colon. The content of fatty acids is generally low in the GI as they normally are rapidly absorbed. However some salts of fatty acids such as calcium salts are known to be excreated in larger amounts. Butyric acid has a molecular weight of 88.11 g/mol, is miscible with water and has pKa of 4.82. At neutral pH it is therefore dissociated making it very soluble.

Cholic acid: Cholic acid is a bile acid, a white crystalline substance slightly soluble in water (175 mg/L). Cholic acid is one of two major bile acids produced by the liver where it is synthesized from cholesterol. Of the two major bile acids, cholate derivatives represent approximately eighty percent of all bile acids. It has a molecular weight of 408.57 g/mol and a pKa of 4.98 which means that it will be inonized at neutral pH. In healthy humans approximately 500 mg is excreted daily in the faeces.

Release Testing

The following setup was used to test the different film coated systems using one or more of the above model chemicals.

The testing of experiments were conducted in a USP Paddle dissolution apparatus at 37° C. Minimum 500 ml of liquid was required to secure proper stirring so this volume was fixed. At the same time the pH was controlled to either 6.8 for colonic conditions by adding a phosphate buffer system at an isotonic level or by using 0.1 N HCl for simulating gastric conditions.

For Phenazone it was found important to fix the relation between the three parameters being amount of Phenazone, amount of activated carbon and concentration of Phenazone. When using 500 ml of release liquid it was necessary to use 6 g of activated carbon for each test to compare with pharmacopeia test. At specified intervals samples were drawn, diluted and tested at 238 nm in a spectrophotometer.

Also when measuring Butyric acid it was important to fix the relation between amount of Butyric acid, amount of activated carbon and concentration of Butyric acid. As for Phenazone, when using 500 ml of release liquid it was also necessary to use 6 g of activated carbon for each test. Two different concentrations of Butyric acid in the release liquid were used: 0.88 g/L or 10 g/L. Butyric acid was quantified at 220 nm.

Indole could not be dissolved to the same high concentration and therefore 100 mg/L was used. 1 g of activated carbon in 500 ml liquid was used for testing to improve the separation power of the test comparing the use of 6 g activated carbon. Indole was quantified at 215 nm.

Cholic acid was not found to be a strong UV absorbent and even at the highest possible concentration (400 mg/L) it was not possible to measure Cholic acid samples directly on the UV spectrophotometer. The samples were therefore measured by HPLC with UV detection at 220 nm (mobile phase: 15% phosphoric acid 0.05M in water/85% Methanol; Column: Kromasil C18; Column temperature: 30° C.; <injection volume: 100 μL). Again 6 g of activated carbon was used for 500 ml of the test solution.

Loss on Drying

Loss of Drying was determined by measuring the evaporation when stored in an oven at 130° C. until constant weight, typically over night. The value was expressed as percentage evaporated from the original mass.

C Results and Discussion

Production of Compositions of the Invention

Compositions according to the invention were made according to the following Tables, in 300 g batches (i.e. 300 g activated carbon):

| Batch | Core | First layer | Second layer |
|---|---|---|---|
| RD1202-19-C2 | Activated carbon Sanded/deburred | 90% ethylcellulose, 10% HPMC Weight increase (thickness) 4% | Aquoat HG Weight increase (thickness) 8% | sharp and apex corners which would be considered difficult to cover uniformly during film coating. RD1202-23-C2 used raw and un-sanded activated carbon. The sanded activated carbon for all batches was fractionated by particle size and only the fraction 0.6 mm to 1.2 mm was used. However, it was subsequently decided that the fraction 0.6 mm to 1.0 mm is preferred.

The first layer for the examples in the Table was 90% ethylcellulose, 10% HPMC, and was applied in ethanol/water by the film coating process described above. The film coating processes all performed well in the STREA fluid-bed without the need for adding plasticizer. Inlet air temperature setpoint for the ethanol:water films was 33° C. Batches were removed after 4% (RD1202-19-C2, RD1202-23-C2) or 6% (RD1202-19-C2) theoretical weight increase.

The second enteric layer was applied to the first layer, also by methods described above. The enteric polymer was Hypromellose-Acetate-Succinate (HPMC-AS; Aqoat HG) dissolving at pH 6.5. Aqoat HG was designed for organic coating (ethanol/water mixture) and can be applied without the addition of plasticizers or lubricants. As the composition was already film coated using organic coatings, organic coating was used. The second layer film was formulated as a 6% solution in ethanol/water 80:20 and applied until 8% weight increase.

More information is given in the following Table:

| | | Batch no | | | |
|---|---|---|---|---|---|
| | | RD1202-19 | RD1202-22 | RD1202-23 | — |
| Inner film | Ethylcellulose (Ethocel 7) | 90% | 90% | 90% | — |
| | Hypromellose (HPMC; Pharmacoat 603) | 10% | 10% | 10% | — |
| | Activated charcoal | Sanded | Sanded | Raw | Sanded |
| | % increase in weight | 4% | 6% | 4% | 0% |
| | Ethanol 96% | 75% | 75% | 75% | — |
| | Purified Water | 25% | 25% | 25% | — |

| | | Batch no | | | |
|---|---|---|---|---|---|
| | | RD1202-19-C2 | RD1202-22-C2 | RD1202-23-C2 | RD1202-24 |
| Enteric coat | Hypromellose-AS (Aqoat HG) | 100% | 100% | 100% | 100% |
| | % increase in weight | 8% | 8% | 8% | 8% |
| | Ethanol 96% | 80% | 80% | 80% | 80% |
| | Purified Water | 20% | 20% | 20% | 20% |

-continued

| Batch | Core | First layer | Second layer |
|---|---|---|---|
| RD1202-22-C2 | Activated carbon Sanded/deburred | 90% ethylcellulose, 10% HPMC Weight increase (thickness) 6% | Aquoat HG Weight increase (thickness) 8% |
| RD1202-23-C2 | Activated carbon Raw (not sanded) | 90% ethylcellulose, 10% HPMC Weight increase (thickness) 4% | Aquoat HG Weight increase (thickness) 8% |

RD1202-19-C2 and RD1202-22-C2 are compositions of the invention and were based on sanded/deburred activated carbon produced by the method described above. The purpose of the sanding process was to round the corner of the activated carbon crystals to allow for the layers/films to cover the corners. Non-sanded activated carbon has very Samples from the Tables above were tested in the release systems described hereinbefore in both acidic conditions and at pH 6.8. Activated carbon was used as a control, as was RD1202-24 which included the sanded activated carbon covered with only the Aqoat enteric layer. Results are presented in the following tables and figures. Note that all samples (but not the controls) are enteric coated on top of the first layer.

Data from Phenazone adsorption tests are given in FIG. 2 and FIG. 3.

In both conditions, uncoated activated carbon adsorbs more than 42% within 5 hours and thereby meets the limit in Ph. Eur.

Samples with only an enteric coating and the batch with non-sanded activated carbon were found to adsorb 5-10% of the Phenazone present within 1 hour in 0.1 M HCl and from that time point not to adsorb further. The adsorption capacity of the activated carbon in compositions of the invention RD1202-19-C2 and RD1202-22-C2 was not released (FIG. 2).

When tested in pH 6.8 the control with the enteric coat only [no ethylcellulose HPMC layer (RD1202-24)] was quickly dissolved and was not found to reduce the adsorption capacity of the activated carbon.

The compositions of the invention [RD1202-19-C2, RD1202-22-C2, RD1202-23-C2] all reduce the release rate of adsorption capacity in phosphate buffer pH 6.8 compared to batch RD1202-24 (see FIG. 3). Two batches were tested twice the same day, and for both of them a good reproducibility in the test was demonstrated (see FIG. 3). The release rate was found to be quicker for the non-sanded batch (RD1202-23-C2) compared to the sanded batch (RD1202-19-C2), indicating problems with a thinner coating on the apexes/points/sharp edges of the non-sanded material, which released the adsorptive capacity more quickly.

Release of adsorption capacity was also found to be influenced by film thickness: the 6% weight increase samples released adsorption capacity a little more slowly than the 4% weight increase samples. The sanded samples did not release 100% of the capacity within 24 hours when tested with Phenazone (about 62% for the 4% samples and 44% for the 6% samples), indicating constant adsorption over a long time (e.g. on a timescale indicative of the time it would take to pass through the gut).

The above results indicate that the compositions of the invention are suitable for use to release the adsorptive capacity of active carbon in the colon following oral administration. As can be seen, the activated carbon is protected at stomach pH (FIG. 2) and the adsorption capacity is slowly released at pH values in the lower intestine and colon (FIG. 3).

Data from Indole adsorption tests are given in FIGS. 4 and 5.

As the amount of Indole was limited by the solubility of Indole, all added Indole was adsorped within 3 hours in both acid and neutral conditions as if no coating was present (FIGS. 4, 5). In acid conditions also samples coated with enteric coating adsorbed this smaller and more lipophilic compound, and 25-40% of the added Indole or capacity of the activated carbon disappeared within two hours.

Changing the pH to 6.8 the enteric coat (RD1202-24) was quickly dissolved and did not reduce the capacity of the activated carbon. Comparing the products of the invention with HPMC containing inner films, the samples containing sanded activated carbon, RD1202-19-C2 and RD1202-22-C2, reduce the release of the adsorptive capacity at pH 6.8, compared to batch RD1202-24; whereas the non-sanded batch release the adsorptive capacity as if no inner coating was present. The two repetitions of the sanded samples from the same test date demonstrated good reproducibility in the test for both formulations, which both released at the same rate in acid.

Thus, the release of adsorptive capacity was again found to be quicker for the non-sanded batch (RD1202-23-C2) compared to the sanded batch (RD1202-19-C2) indicating problems with thinner coating on the apexes of the non-sanded material.

Release rate was again found to be influenced by film thickness as the 6% weight increase samples released a little slower than the 4% weight increase samples.

All tested samples released 100% of the adsorption capacity within 24 hours.

The above results indicate that the compositions of the invention are are suitable for use to release the adsorptive capacity of active carbon in the colon following oral administration. As can be seen, the activated carbon is protected at stomach pH (FIG. 4) and the adsorption capacity is slowly released at pH values in the lower intestine and colon (FIG. 5).

Data from butyric acid adsorption tests are given in FIGS. 6 and 7.

In acid conditions the HPMC containing films let the activated carbon adsorb 10-15% of the Butyric acid in two hours, which corresponded to 50% of the capacity (FIG. 6). This is not considered a problem because short chain acids are not found in the stomach (they are produced in vivo by bacteria fermentation in colon)

Changing the pH to 6.8 (FIG. 7) the enteric coat (RD1202-24) was dissolved over three hours and the total capacity of the activated carbon released.

In general, release of adsorption capacity was faster in acid conditions compared to neutral conditions which was surprising because the products were enteric coated and were supposed to hold tight in acid condition. However, it must be concluded that the undissociated Butyric acid molecule penetrates the films better than the ionic form at neutral pH. Comparing the products of the invention with HPMC containing inner films, all of them again reduced the release of adsorption capacity at pH 6.8 compared to batch RD1202-24. Again two of the samples were tested twice, and for one of them good reproducibility in the test was demonstrated. Some variation was found for the other sample.

The release rate was again found to be quicker for the non-sanded batch (RD1202-23-C2) compared to the sanded batch (RD1202-19-C2) indicating problems with thinner coating on the apexes of the non-sanded material.

Also, the release rate was again found to be influenced by film thickness as the 6% weight increase samples released a little slower than the 4% weight increase samples.

The above results indicate that the compositions of the invention are suitable for use to release the adsorptive capacity of active carbon in the colon following oral administration. As can be seen, for compositions of the invention, the adsorption capacity is slowly released at pH values in the lower intestine and colon (FIG. 7).

Data from Cholic acid adsorption tests are given in FIGS. 8 and 9.

In acid conditions only a small part of the capacity was released in two hours (~7%) and there is almost no difference between the samples.

Changing the pH to 6.8 reduced the adsorption rate on the uncoated activated carbon but not the capacity. The enteric film (batch RD1202-24) was dissolved with time and the capacity released, but it took several hours.

Comparing with the test of samples without enteric coating (not shown) data, were found very similar; and the enteric coat was not found to reduce or delay the adsorption. Only for the 6% film coated sample (RD1202-22-C2) a small delay in release of adsorptive capacity was observed, differentiating this sample form the 4% film coated sample (RD1202-19-C2).

The above results indicate that the compositions of the invention are suitable for use to release the adsorptive capacity of active carbon in the colon following oral administration. As can be seen, the adsorption capacity is slowly released at pH values in the lower intestine and colon (FIG. 7).

CONCLUSION

The above results indicate that compositions of the invention would provide prolonged adsorption of various components by activated carbon at pH values found in the colon, following removal of the enteric layer. Further, the compositions of the invention are protected at stomach pH by the enteric layer so will not adsorb of nutrients etc. higher up the GI tract. This is indicative that compositions of the invention will provide effective adsorption by activated carbon (e.g. to treat fistula or other medical condition) in vivo, without the problems of the known oral formulations. It further indicates that compositions of the invention may retain some adsorptive capacity (that is have some residual adsorptive power) all the way through the G I tract and into the rectum and anus. The retention of adsorptive capacity of activated carbon throughout the lower intestine and colon is important because the exact location of the fistula may not be known and/or because it may be difficult to target the exact site of the fistula. Other medical conditions may be more effectively treated using the formulations of the invention, which may effectively and steadily release the adsorptive capacity of activated carbon throughout the lower intestine, colon etc.

The results also indicate that the performance of the compositions of the invention (e.g. where the adsorptive capacity is released, how long adsorptive capacity is maintained etc.) may be varied by adjusting the compositions, thicknesses etc of the first and second layers. Variations of this nature, which are within the scope of the invention, would be readily understood by the skilled person.

The compositions described above (e.g. RD1202-19-C2 and RD1202-22-C2) are suitable for oral administration e.g. as a powder, granules or suspension to treat gastrointestinal fistula (e.g. fistula of the small intestine, fistula of the large intestine, anorectal fistula). In another example the coated particles (granules) may be formulated as a tablet or in a capsule, or as granules (e.g. in a container such as a sachet) for the patient to swallow (e.g. with water).

Example A—Adsorption of Indole and Indole Related Compounds

Indole is an aromatic heterocyclic organic compound. Indole can be produced by bacteria as a degradation product of the amino acid tryptophan, and this takes place mainly in the colon. Indole therefore occurs naturally in human feces, and is present at levels of approximately 100 mg/l. Indole has an intense fecal odor.

A male human subject took two doses (each of 3 to 4 g) of the following formulation A, a composition according to the invention, per day for 5 days.

| Batch | Core | First layer | Second layer |
| --- | --- | --- | --- |
| Formulation A | Activated carbon Sanded/deburred | 90% ethylcellulose, 10% HPMC Weight increase (thickness) 4% | Aquoat HG Weight increase (thickness) 8% |

The formulation was exactly as described for batch RD1202-19-C2 above.

It was found that the smell of the patient's stool was greatly reduced or even completely removed following administration of the formulation of the invention. This is indicative of removal of indole and indole related compounds from the stool. As indicated above, indole is produced mainly in the colon. The results of this test indicate that the activated carbon had removed (adsorbed) the indole (and related compounds) from the stool, which is indicative that in vivo the formulation of the invention retained adsorptive capacity at least until the colon.

Example

Oral Formulation

Activated carbon particles made from coconut shells are milled down to granules of particle size 0.2 mm to 2.0 mm). These individual particles (granules) are each coated with an inner coating (insoluble semipermeable membrane) comprising a mixture of Eudragit RS 30 D and Eudragit RL 30 D, which is applied by methods well known in the art (e.g. the methods of U.S. Pat. No. 6,632,454 B2). The individual coated activated carbon particles (granules) are then each coated with an outer enteric coating comprising Eudragit FS 30 D, again by methods well known in the art (e.g. the methods of U.S. Pat. No. 6,632,454 B2), to provide an oral formulation.

The oral formulation is suitable for oral administration e.g. as a powder or suspension to treat gastrointestinal fistula (e.g. fistula of the small intestine, fistula of the large intestine, anorectal fistula). In another example the coated particles (granules) may be formulated as a tablet or in a capsule.

APPENDIX I

The detailed settings for the digital image analysis software (Media Cybernetics Image Pro-Plus version 6.1.0.346).

```
Sub Corners1( )
'<c>J
    Dim m As Integer
    Dim num As Integer
    Dim fil As String * 255
    ret = IpDocGet(GETNUMDOC, 0, num)
    For m = 0 To num-1
        ret = IpAppSelectDoc(m)
        ret = IpBlbShow(1)
        ret = IpSegSetRange(1, 0, 70)
        ret = IpSegPreview(CURRENT_C_T)
        ret = IpBlbSetRange(0, 70)
        ret = IpBlbEnableMeas(BLBM_AREA,1)
        ret = IpBlbSetFilterRange(BLBM_AREA, 75, 10000000)
        ret = IpSegShow(0)
        ret = IpBlbCount( )
        ret = IpBlbUpdate(0)
        ret = IpDcSet(DC_AUTO, 0)
        ret = IpDcUpdate(DC_FETCH)
    Next
End Sub
Sub Corners2( )
    Dim fil As String * 255
    Dim m As Integer
    Dim num As Integer
    Dim mask1 As Integer
    Dim mask2 As Integer
    Dim mask3 As Integer
    ret = IpDocGet(GETNUMDOC, 0, num)
    For m = 0 To num-1
        ret = IpAppSelectDoc(m)
        ret = IpDocGetStr(INF_FILENAME, DOCSEL_ACTIVE, fil)
        ret = IpBlbShow(1)
        ret = IpBlbSetAttr(BLOB_AUTORANGE, 0)
        ret = IpSegSetRange(1, 0, 70)
        ret = IpSegPreview(CURRENT_C_T)
        ret = IpBlbSetRange(0, 70)
        ret = IpBlbEnableMeas(BLBM_AREA,1)
        ret = IpBlbSetFilterRange(BLBM_AREA, 75, 1000000)
        ret = IpSegShow(0)
        ret = IpBlbCount( )
        ret = IpBlbUpdate(0)
        ret = IpBlbCreateMask( )
        ret = IpDocGet(GETACTDOC, 0, mask1)
        ret = IpAppSelectDoc(m)
        ret = IpFltClose(MORPHO_2x2SQUARE, 6)
```

APPENDIX I-continued

The detailed settings for the digital image analysis software
(Media Cybernetics Image Pro-Plus version 6.1.0.346).

```
    ret = IpBlbCount( )
    ret = IpBlbUpdate(0)
    ret = IpBlbCreateMask( )
    ret = IpDocGet(GETACTDOC, 0, mask2)
    ret = IpOpImageLogic(mask1, OPL_XOR, 1)
    ret = IpDocGet(GETACTDOC, 0, mask3)
    ret = IpFltOpen(MORPHO_2x2SQUARE, 1)
    fil = Replace$(fil,".bmp", " corners.bmp")
    ret = IpWsSaveAs(fil, "bmp")
    ret = IpBlbSetAttr(BLOB_AUTORANGE, 1)
    ret = IpBlbSetAttr(BLOB_BRIGHTOBJ, 1)
    ret = IpBlbEnableMeas(BLBM_AREA,1)
    ret = IpBlbSetFilterRange(BLBM_AREA, 2, 250)
    ret = IpBlbCount( )
    ret = IpBlbUpdate(0)
    ret = IpDcSet(DC_AUTO, 0)
    ret = IpDcUpdate(DC_FETCH)
    ret = IpDocClose( )
    ret = IpAppSelectDoc(mask1)
    ret = IpDocClose( )
    ret = IpAppSelectDoc(mask2)
    ret = IpDocClose( )
    ret = IpAppSelectDoc(m)
    ret = IpDocClose( )
    ret = IpAnShow(0)
    ret = IpCMMShow(CMM_W_CONVERT,0)
    ret = IpBlbShow(0)
    ret = IpFltShow(0)
    ret = IpOpShow(0)
  Next
End Sub
```

Numbered Statements

There have been disclosed hereinbefore the compositions, uses and methods defined by the following numbered paragraphs:

1. A composition comprising:
   (a) a core comprising activated carbon;
   (b) a first layer around the core, the first layer comprising an insoluble semipermeable material; and
   (c) a second layer around the first layer which dissolves at a predetermined pH.

2. A composition according to paragraph 1 wherein the core is activated carbon.

3. A composition according to paragraph 1 or 2 wherein the first layer allows gradual diffusion of molecules through the semipermeable membrane towards the core into contact with the activated carbon.

4. A composition according to paragraph 1, 2 or 3 wherein the first layer comprises a mixture of copolymers composed of 85 to 98% by weight free-radical polymerized $C_1$- to $C_4$-alkyl esters of acrylic or methacrylic acid and 15 to 2% by weight (methy) acrylate monomers with a quaternary ammonium group in the alkyl radical.

5. A composition according to any preceding paragraph wherein the first layer comprises a copolymer comprising 65% by weight methyl methacrylate, 30% by weight ethyl acrylate and 5% by weight 2-trimethylammoniummethyl methacrylate chloride.

6. A composition according to paragraph 1, 2 or 3 wherein the first layer comprises a mixture of copolymers composed of 85 to less than 93% by weight free-radical polymerized $C_1$- to $C_4$-alkyl esters of acrylic or methacrylic acid and 15 to more than 7% by weight 2-trimethylammoniummethyl methacrylate chloride.

7. A composition according to any of paragraphs 1, 2 or 6 wherein the first layer comprises a copolymer comprising 60% by weight methyl methacrylate, 30% by weight ethyl acrylate and 10% by weight 2-trimethylammoniummethyl methacrylate chloride.

8. A composition according to any preceding paragraph wherein the first layer comprises a mixture of a first copolymer comprising 65% by weight methyl methacrylate, 30% by weight ethyl acrylate and 5% by weight 2-trimethylammoniummethyl methacrylate chloride and a second copolymer comprising 60% by weight methyl methacrylate, 30% by weight ethyl acrylate and 10% by weight 2-trimethylammoniummethyl methacrylate chloride.

9. A composition according to any preceding paragraph wherein the second layer comprises a material which dissolves at pH 5 to pH 7.

10. A composition according to any preceding paragraph wherein the second layer is an enteric layer comprising a material which remains substantially intact at pH 1 to 4.9, but which breaks down rapidly at pH 5 to 7.

11. A composition according to any preceding paragraph wherein the second layer is a pH sensitive polymer.

12. A composition according to any preceding paragraph wherein the second layer comprises a copolymer composed of 80 to 95% by weight free-radical polymerized $C_1$- to $C_4$-alkyl esters of acrylic or methacrylic acid and 5 to 25% by weight (meth)acrylate monomers with an anionic group in the alkyl radical.

13. A composition according to any preceding paragraph wherein the second layer comprises a (meth)acrylate copolymer comprising 10 to 30% by weight methyl methacrylate, 50 to 70% by weight methyl acrylate and 5 to 15% by weight methacrylic acid.

14. A composition according to any preceding paragraph wherein the activated carbon is of particle size 0.05 to 2.1 mm.

15. A composition according to any preceding paragraph wherein the activated carbon is the sole active pharmaceutical ingredient.

16. A composition according to any preceding paragraph for use in the treatment of fistula, or for use in the manufacture of a medicament for the treatment of fistula.

17. A method of treatment of fistula, comprising a step of administering (e.g. orally) to a patient in need thereof a composition comprising:
   (a) a core comprising (e.g. which is) activated carbon;
   (b) a first layer around the core, the first layer comprising an insoluble semipermeable material; and
   (c) a second layer around the first layer which dissolves at a predetermined pH.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. An oral pharmaceutical composition comprising coated activated carbon comprising:
   (a) a core consisting of activated carbon, wherein the activated carbon is sanded or deburred;
   (b) a first layer around the core, wherein the first layer forms an insoluble semipermeable membrane around the core, and comprises a material which is insoluble in water and, optionally, a water soluble material in an amount of from 0.1 to 30% by weight of the amount of the insoluble material; and (c) a second layer around the first layer which dissolves at a pH of from 5 to 7, wherein, upon dissolution of the second layer, the first layer allows gradual diffusion of molecules through the semipermeable membrane towards the core into contact with the activated carbon of the core and retains substantially all of the activated carbon within the semipermeable membrane.

2. The pharmaceutical composition according to claim 1, wherein the activated carbon has a particle size of from 0.02 to 5.0 mm.

3. The pharmaceutical composition according to claim 1, wherein the insoluble material comprises one or more selected from the group consisting of ethyl cellulose, glycerylmonostearate, cellulose acetate butyrate, dipolylactic acid, polyvinyl chloride, and poly(meth)acrylate polymers.

4. The pharmaceutical composition according to claim 1, wherein the first layer further comprises the water soluble material.

5. The pharmaceutical composition according to claim 4, wherein the water soluble material comprises hydroxypropylmethyl cellulose (HPMC).

6. The pharmaceutical composition according to claim 5, wherein the water soluble material is mixed with the insoluble material.

7. The pharmaceutical composition according to claim 5, wherein the water soluble material is present in an amount of from 5 to 15% by weight of the amount of the insoluble material.

8. The pharmaceutical composition according to claim 1, wherein the second layer is an enteric layer comprising a material which remains substantially intact at pH 1 to 4.9, and breaks down rapidly at a pH of from 5 to 7.

9. The pharmaceutical composition according to claim 1, wherein the second layer comprises a pH sensitive polymer.

10. The pharmaceutical composition according to claim 1, wherein the second layer comprises a polymer selected from the group consisting of hypromellose acetate succinate, cellulose acetate trimellitate (CAT), cellulose acetate phthalate (CAP), anionic copolymers based on methylacrylate, methylmethacrylate and methacrylic acid, hydroxypropyl methylcellulose phthalate (HPMCP), hydroxypropylmethylcellulose acetate succinate (HPMCAS), copolymers of methacrylic acid and ethyl acrylate, copolymers of methacrylic acid and methyl methacrylate copolymers (1:1 ratio), copolymers of methacrylic acid and methyl methacrylate (1:2 ratio), polyvinyl acetate phthalate (PVAP), and shellac resins.

11. The pharmaceutical composition according to claim 1, wherein the activated carbon is the sole active pharmaceutical ingredient present in the composition.

12. The pharmaceutical composition according to claim 1, wherein
the first layer comprises ethyl cellulose, and optionally further comprises hydroxypropylmethylcellulose (HPMC); and
the second layer comprises hydroxypropylmethylcellulose acetate succinate (HPMC AS).

13. The pharmaceutical composition according to claim 1, wherein the activated carbon has a particle size of from 0.6 to 1.2 mm.

14. The pharmaceutical composition according to claim 5, wherein the water soluble material is present in an amount of 2 to 25% by weight of the amount of the insoluble material.

15. A method of administering activated carbon to a subject in need thereof, comprising orally administering a pharmaceutical composition according to claim 1 to the subject, wherein the subject is suffering from a condition selected from the group consisting of gastrointestinal (GI) dysfunction, GI diseases, malfunction of the GI tract, fistula, Irritable Bowel Disease (IBD), ulcerative colitis, Crohn's disease, Irritable Bowel Syndrome (IBS), poisoning, or wherein the subject has been or is being treated with another pharmaceutical composition associated with a presence or build-up of the other pharmaceutical composition and/or its metabolite(s) in the lower ileum, colon or caecum, and the method reduces the presence of the other pharmaceutical composition and/or its metabolite(s) in the lower ileum, colon or caecum of the subject.

16. The method according to claim 15, wherein the other pharmaceutical composition and/or its metabolites are selected from the group consisting of antibiotics, irinotecan, and the metabolite SN38.

17. An oral pharmaceutical composition comprising coated activated carbon comprising:

(a) a core consisting of activated carbon, wherein the activated carbon is sanded or deburred;

(b) a first layer around the core, wherein the first layer forms an insoluble semipermeable membrane around the core, and comprises a material which is insoluble in water and, optionally, a water soluble material in an amount of from 0.1 to 30% by weight of the amount of the insoluble material; and (c) a second layer around the first layer which dissolves at a predetermined location in the gastrointestinal tract, wherein, upon dissolution of the second layer, the first layer allows gradual diffusion of molecules through the semipermeable membrane towards the core into contact with the activated carbon of the core and retains substantially all of the activated carbon within the semipermeable membrane.

18. The pharmaceutical composition according to claim 17, wherein the second layer comprises a material which dissolves at a pH of from 5 to 7.

* * * * *